United States Patent [19]

Ehrenfreund et al.

[11] Patent Number: 4,952,599
[45] Date of Patent: Aug. 28, 1990

[54] PHENYLTHIOUREAS, PHENYLISOTHIOUREAS, PHENYLCARBODIIMIDES, PESTICIDAL COMPOSITIONS CONTAINING THEM AND THEIR USE IN PEST CONTROL

[75] Inventors: Josef Ehrenfreund, Allschwil, Switzerland; Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 221,849

[22] Filed: Jul. 20, 1988

[30] Foreign Application Priority Data

Jul. 29, 1987 [CH] Switzerland .......................... 2910/87
Jun. 2, 1988 [CH] Switzerland .......................... 2092/88

[51] Int. Cl.$^5$ .................. C07D 249/12; C07D 277/36; C07D 285/08; C07D 185/12
[52] U.S. Cl. ................................. 514/363; 514/367; 514/369; 514/375; 514/376; 514/387; 514/384; 514/381; 514/400; 514/407; 514/418; 514/424; 514/445; 514/470; 514/471; 548/136; 548/144; 548/169; 548/171; 548/129; 548/186; 548/187; 548/189; 548/221; 548/263.8; 548/264.2
[58] Field of Search ............... 548/187, 186, 189, 263, 548/265, 136, 129, 221, 171, 169; 514/369, 384, 363, 445, 375, 367, 400, 471, 424, 407, 376, 470, 418, 387, 381

[56] References Cited

FOREIGN PATENT DOCUMENTS 105735  4/1984  European Pat. Off. .
202807  3/1988  European Pat. Off. .
2060626 5/1981  United Kingdom .

Primary Examiner—Robert Gerstl
Attorney, Agent, or Firm—Edward McC. Roberts

[57] ABSTRACT

Novel substituted phenylthioureas, phenylisothioureas and phenylcarbodiimides of formula I

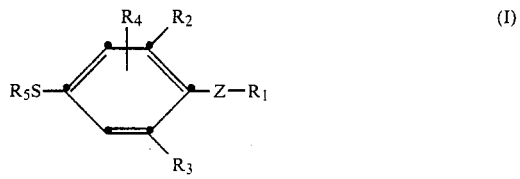

wherein $R_1$ is $C_1-C_{10}$alkyl, unsubstituted or substituted by one or more halogen atoms and/or $C_1-C_6$alkoxy groups; $C_3-C_6$alkenyl, $C_3-C_8$cycloalkyl, $C_3-C_8$cycloalkyl which is substituted by one or more halogen atoms and/or $C_1-C_4$alkyl groups; $C_3-C_8$cycloalkyl-$C_1$-$C_4$alkyl, di($C_3-C_8$)cycloalkyl-$C_1$-$C_4$alkyl; $C_1$-$C_4$phenylalkyl or $C_1$-$C_4$phenylalkyl which is substituted in the phenyl nucleus by one or more members selected from the group consisting of halogen, $C_1$-$C_4$alkyl, $C_1$-$C_4$alkoxy and/or $C_1$-$C_4$haloalkyl; or is $C_5$-$C_6$cycloalkenyl, $R_2$ is hydrogen, $C_1$-$C_5$alkyl or $C_5$-$C_6$cycloalkenyl,
$R_3$ is $C_1$-$C_5$alkyl or $C_5$-$C_6$cycloalkenyl,
$R_4$ is hydrogen or $C_1$-$C_3$alkyl,
$R_5$ is a 5-membered heterocycle containing 1 to 4 identical or different hetero atoms selected from the group consisting of N, O and S, or is a heterocycle which is substituted by one or more members selected from the group consisting of halogen, $C_1$-$C_4$alkyl, $C_1$-$C_4$alkoxy, $C_1$-$C_4$haloalkyl, $C_1$-$C_4$haloalkoxy, $C_1$-$C_4$alkylthio and/or phenyl or substituted phenyl, and which contains 1 to 4 identical or diffenent hetero atoms selected from the group consisting of N, O and S,
Z is —NH—CS—NH—, —N=C(SR$_6$)—NH— or —N=C=N—, and
$R_6$ is $C_1$-$C_5$alkyl, $C_2$-$C_5$alkenyl, $C_3$-$C_4$alkynyl, $C_1$-$C_4$alkoxy-$C_1$-$C_4$alkyl or $C_1$-$C_4$alkylthio-$C_1$-$C_4$alkyl and to salts thereof, to the preparation of these compounds and to intermediates for their synthesis. The invention further relates to the use of the novel compounds in pest control and to pesticidal compositions which contain at least one compound of formula I. The preferred utility is the control of pests of animals and plants.

12 Claims, No Drawings

PHENYLTHIOUREAS, PHENYLISOTHIOUREAS, PHENYLCARBODIIMIDES, PESTICIDAL COMPOSITIONS CONTAINING THEM AND THEIR USE IN PEST CONTROL

The present invention relates to novel substituted phenylthioureas, phenylisothioureas and phenylcarbodiimides which are linked to a 5-membered heterocycle through a sulfur bridge, to salts thereof with organic and inorganic acids, to their preparation and to intermediates for their preparation. The invention further relates to pesticidal compositions which contain these compounds and to the use thereof in pest control.

The compounds of this invention have the formula I

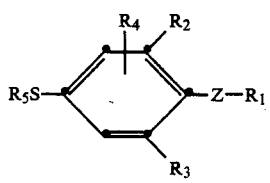

wherein $R_1$ is $C_1$-$C_{10}$alkyl, unsubstituted or substituted by one or more halogen atoms and/or $C_1$-$C_6$alkoxy groups; $C_3$-$C_6$alkenyl, $C_3$-$C_8$cycloalkyl, $C_3$-$C_8$cycloalkyl which is substituted by one or more halogen atoms and/or $C_1$-$C_4$alkyl groups; $C_3$-$C_8$cycloalkyl-$C_1$-$C_4$alkyl, di($C_3$-$C_8$)cycloalkyl-$C_1$-$C_4$alkyl; $C_1$-$C_4$phenyklalkyl or $C_1$-$C_4$phenylalkyl which is substituted in the phenyl nucleus by one or more members selected from the group consisting of halogen, $C_1$-$C_4$alkyl, $C_1$-$C_4$alkoxy and/or $C_1$-$C_4$haloalkyl; or $C_5$-$C_6$cycloalkenyl, $R_2$ is hydrogen, $C_1$-$C_5$alkyl or $C_5$-$C_6$cycloalkyl, $R_3$ is $C_1$-$C_5$alkyl or $C_5$-$C_6$cycloalkyl, $R_4$ is hydrogen or $C_1$-$C_3$alkyl, $R_5$ is a 5-membered heterocycle containing 1 to 4 identical or different hetero atoms selected from the group consisting of N, O and S, or is a heterocycle which is substituted by one or more members selected from the group consisting of halogen, $C_1$-$C_4$alkyl, $C_1$-$C_4$alkoxy, $C_1$-$C_4$Haloalkyl, $C_1$-$C_4$haloalkoxy, $C_1$-$C_4$alkylthio and/or phenyl or substituted phenyl, and which contains 1 to 4 identical or different hetero atoms selected from the group consisting of N, O and S, Z is —NH—CS—NH—, —N=C(SR$_6$)—NH— or —N=C=N—, and $R_6$ is $C_1$-$C_5$alkyl, $C_2$-$C_5$alkenyl, $C_3$-$C_4$alkynyl, C $C_1$-$C_4$alkylthio -$C_1$-$C_4$alkyl.

Suitable halogen substituents are fluorine and chlorine as well as bromine and iodine. Fluorine and chlorine are preferred.

Alkyl groups can be straight chain or branched. Such alkyl groups may be, for example, methyl, ethyl, propyl, isopropyl, butyl, isobutyl, secbutyl, tert-butyl or pentyl, hexyl, octyl and the like, and isomers thereof.

Alkenyl groups can be straight chain or branched and contain one or more double bonds. Examples of such alkenyl groups comprise vinyl, allyl, 1-propenyl, isopropenyl, allenyl, butenyls, pentenyls or hexenyls.

Alkynyl groups can be straight chain or branched and are, for example, 1-propynyl, 2-propynyl or the different butynyl forms.

Phenylalkyl groups can be straight chain or branched and are, typically, benzyl, phenethyl, phenpropyl, phenisopropyl or phenbutyl and the isomers thereof. If the phenyl nucleus is substituted, then the above definitions apply to the halogens and to the alkyl, alkoxy and haloalkyl groups.

Suitable $C_1$-$C_{10}$alkyl substituents which are substituted by one or more halogen atoms and/or $C_1$-$C_6$alkoxy groups can be straight chain or branched and be only partially halogenated or also prehalogenated and/or be substituted by 1 to 5 $C_1$-$C_6$alkoxy groups, the halogen and alkyl substituents being as defined above. Typical examples of such substituents are methyl which is substituted by 1 to 3 fluorine, chlorine and/or bromine atoms, for example $CH_2$ or $CF_3$; ethyl which is substituted by 1 to 5 fluorine, chlorine and/or bromine atoms, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each substituted by 1 to 7 fluorine, chlorine and/or bromine atoms, for example $CH_2CHBrCH_2Br$, $CF_2CHFCF_3$, $CH_2CF_2CF_3$ or $CH(CF_3)_2j$ butyl an isomer thereof which is substituted by 1 to 9 fluorine, chlorine and/or bromine atoms, for example $CF(CF_3)CHFCF_3$ or $CH_2(CF_2)_2CF_3$; methoxymethyl, methoxyethyl, ethoxyethyl, methoxypropyl, ethoxypropyl, propoxypropyl, methoxybutyl, ethoxybutyl, propoxybutyl or butoxybutyl, 1,2-dimethoxyethyl, 1,3-dimethoxyethyl, 1,3-dimethoxypropyl or 2,4-dimethoxybutyl. These definitions also apply by analogy to the unsubstituted or mono- to perhalogenated alkyl groups.

Cycloalkylene and cycloalkenyl groups may be, for example, cyclopropyl, cyclobutyl, cyclopentyl, cyclopentenyl, cyclohexyl or cyclohexenyl. The cycloalkyl groups can be substituted by one or more $C_1$-$C_4$alkyl groups and/or be linked to the remainder of the molecule through a $C_1$-$C_4$alkylene bridge.

suitable 5-membered heterocycles are:

$Q_1$=thiazolyl, $Q_1$=1,2,4-thrazolyl, $Q_2$=1,3,4-thiadiazolyl, $Q_4$=1,2,4 thiadiazolyl, $Q_5$=1,3,4-oxadiazolyl, $Q_6$=thienyl, $Q_7$=benzoxalyl, $Q_8$=benzthiazolyl, $Q_9$imidazolyl, $Q_{10}$=furanyl, $Q_{11}$=pyrrolyl, $Q_{12}$=pyrazolyl, $Q_{13}$=oxaxolyl, $Q_{14}$=benzofuranyl, $Q_{15}$=indolyl, $Q_{16}$=benzimidazolyl and $Q_{17}$=tetrazolyl.

Representative examples are:

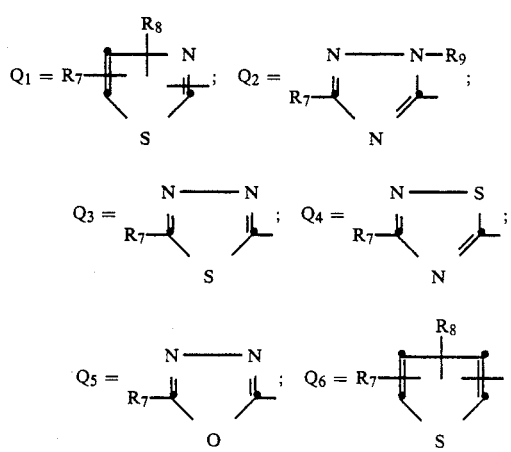

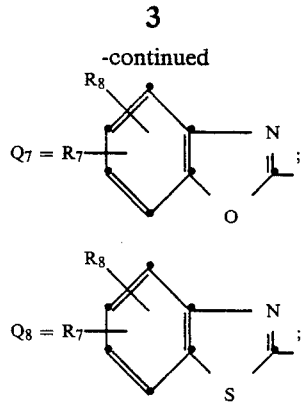

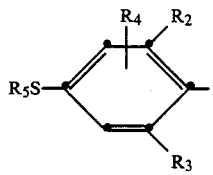

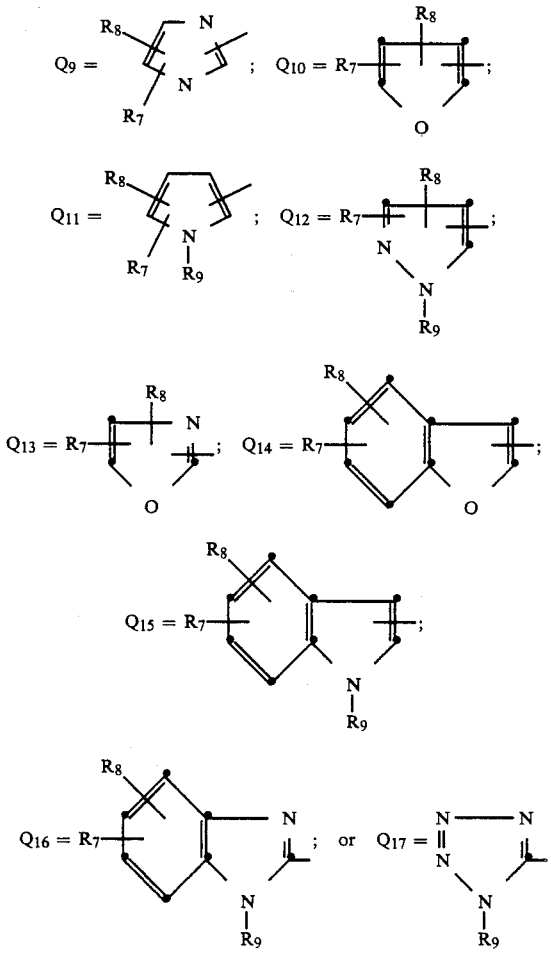

in which formulae $R_7$ and $R_8$ are each hydrogen, halogen, $C_1-C_4$alkyl, $C_1-C_4$alkoxy, $C_1-C_4$haloalkyl, $C_1-C_4$haloalkoxy, $C_1-C_4$alkylthio, phenyl or phenyl which is substituted by one or more members selected from the group consisting of $C_1-C_4$alkyl, $C_1-C_4$alkoxy and/or haloalkyl; and $R_9$ is hydrogen or $C_1-C_4$alkyl.

Compounds of formula I, wherein Z is $-N=C(SR_6)-NH-$, can also be in the form of acid addition salts. Acids suitable for forming such salts are organic as well as inorganic acids. Examples of such acids are: hydrochloric acid, hydrobromic acid, hydriodic acid, nitric acid, different phosphoric acids, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acid and salicylic acid.

Compounds of formula I, wherein Z is $-N=C(SR_6)-NH-$, can be obtained in their tautomeric forms

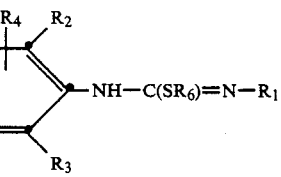

The invention encompasses the individual tautomers as well as mixtures of tautomers.

Preferred compounds of formula I are those wherein $R_1$ is $C_1-C_7$alkyl, $C_1-C_7$alkyl which is substituted by one ore more halogen atoms and/or $C_1-C_5$alkoxy groups; $C_5-C_6$cycloalkyl, $C_3-C_5$cycloalkyl-$C_1-C_3$alkyl or di($C_3-C_5$)cycloalkyl-$C_1-C_3$alkyl; $R_2$ is $C_1-C_4$alkyl or $C_5-C_6$cycloalkyl; $R_3$ is $C_1-C_4$alkyl; $R_4$ is hydrogen; $R_5$ is

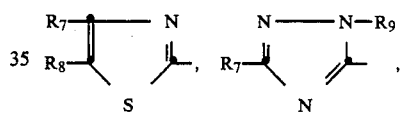

wherein $R_7$ and $R_8$ are each hydrogen, chlorine, bromine, $C_1-C_4$alkyl or $C_1-C_4$haloalkyl, and $R_9$ is $C_1-C_5$alkyl; Z is $-NH-CS-NH-$, $-N=C(SR_6)-NH-$ or $-N=C=N-$; and $R_6$ is $C_1-C_5$alkyl.

Among these compounds, those compounds of formula I are preferred in which (a) $R_1$ is $C_3-C_5$alkyl or $C_5-C_6$cycloalkyl; $R_2$ and $R_3$ are each $C_1-C_4$alkyl; $R_4$ is hydrogen; $R_5$ is

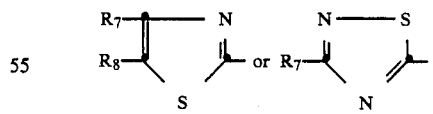

wherein $R_7$ and $R_8$ are each chlorine, bromine or methyl; and Z is $-NH-CH-NH-$; or (b) $R_1$ is $C_3-C_5$alkyl or $C_5-C_6$cycloalkyl; $R_2$ and $R_3$ are each $C_1-C_4$alkyl; $R_4$ is hydrogen; $R_5$ is

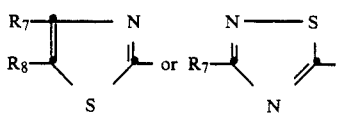

wherein R₇ and R₈ are each chlorine, bromine or methyl; Z is —N=C(SR₆)—NH—; and R₆ is methyl or ethyl; or (c) R₁ is C₃–C₅alkyl or C₅–C₆cycloalkyl; R₂ and R₃ are each C₁–C₄alkyl; R₄ is hydrogen; R₅ is

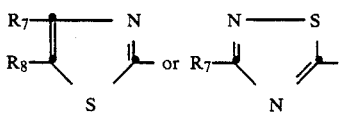

wherein R₇ and R₈ are each chlorine, bromine or methyl; and Z is —N=C=N—.

The compound of formula I of this invention can be prepared by methods which are known per se, for example by (A) reacting an isothiocyanate for formula II

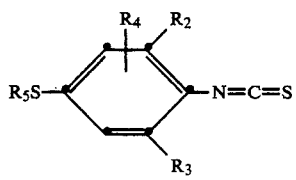

with an amine of formula III

     (III)

to give the thiourea and, if desired, (B) reacting the resulting thiourea with a compound of formula IV

     (IV)

to give the isothiorea, or (C) converting the resultant thiorea into the carbodiimide by removal of hydrogen sulfide. In the formulae above, R₁, R₂, R₃, R₄, R₅ and R₆ have the given meanings and X is a suitable leaving group, for example a halogen atom, preferably a chlorine, bromine or iodine atom, or is a sulfate or halogenated or alkylated sulfate, for example a tosylate, brosylate or mono- or dialkylsulfate (mesylate, dimethyl sulfate).

Process (A) is usually carried out under normal pressure and in the presence of an organic solvent or diluent. The reaction temperature is in the range from 0° to 150° C., preferably from 10° to 70° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorobenzene; nitriles such as acetonitrile or propionitrile; and ketones, such as acetone, methyl ethyl ketone, methyl isopropyl ketone, methyl isobutyl ketone and cyclohexanone.

Process (B) is conveniently carried out in an inert organic solvent and under slightly elevated or normal pressure. The reaction temperature is in the range from 10° to 250° C., but is preferably the boiling temperature of the solvent employed or from 50° to 150° C. Examples of suitable solvents or diluents are: ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; alcohols or dimethyl formamide. The reaction is either carried out in the presence of a base or the resultant salt is subsequently treated with a base (q.v. J. B. Hendricksen et al., "Organic Chemistry", McGraw Hill Book Co., 1970, pp. 378-382).

Process (C) is conveniently carried out in an aprotic organic solvent or diluent and under normal pressure. The reaction temperature is in the range from 0° to 150° C., preferably from 10° to 50° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorobenzene; nitriles such as acetonitrile and propionitrile; and ketones, e.g. acetone methyl ethyl ketone, methyl isopropyl ketone, methyl isobutyl ketone and cyclohexanone. The removal of hydrogen sulfide is effected by methods which are described in the literature [T. Shibanuma, Chemistry Letters (1977), pp. 575-6; S. Kim, tetrahedron Letters (1985), pp. 1661-1664; W. Weith, B. 6 (1873) 1398; G. Amiard, Bull. Soc. Chim. 1956, 1360]. Suitable reagents for the elimination reactions are e.g. HgO, specific pyridinium salts, chloroacetates, cyanuric chloride, p-toluenesulfochloride or specific phosphate derivatives.

The isothiocyanates of formula II can be prepared by methods which are known per se, for example by thiophosgenating an aniline of formula V

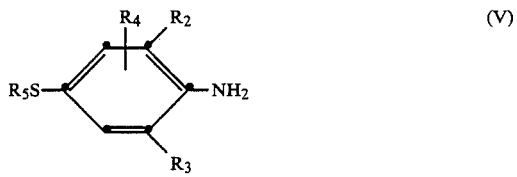

wherein R₂, R₃, R₄ and R₅ are as defined for formula I.

The process for the preparation of the compounds of formula II is conveniently carried out in the presence of an inert solvent or diluent in the temperature range from 0° to 100° C. under normal pressure. Suitable solvents and diluents are, for example, ethers or ethereal compounds such as diethyl ether, diisopropyl ether, dioxane or tetrahydrofuran; aromatic hydrocarbons such as benzene, toluene or xylenes; ketone such as acetone, methyl ethyl ketone or cyclohexanone; or chlorinated hydrocarbons such as dichloromethane or tetrachloromethane.

Suitable bases are organic or inorganic bases such as sodium hydride, sodium or calcium carbonate, tertiary amines such as triethylamine, triethylenediamine or 4-dimethylaminopyridine, or pyridine.

Another means of preparing the isothiocyanates of formula II is via the corresponding thiourea which is unsubstituted at one nitrogen. This process comprises reacting an aniline of formula V with ammonium thiocyanate, in acidic medium preferably containing a mineral acid, to give the corresponding thiourea which, in turn, splits off ammonia on being heated to 130°-200° C. and is converted into an isothiocyanate of formula II (q.v. Saul Patai, "The Chemistry of Cyanates and their Thio Derivatives", John Wiley and Sons, 1977, p. 1032 et seq.; Chemistry and Industry, July 3, 1954, p. 735, J.

N. Baxter et al., "New method of preparation of aryl isothiocyanates").

The anilines of formula V can, in turn, be prepared by methods which are known per se, for example by reacting a mercaptoaniline of formula VI

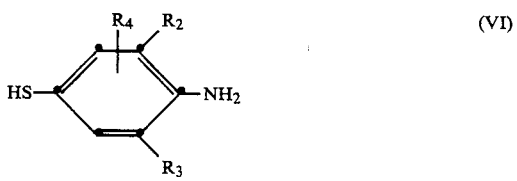

with a compound of formula VII $$R_5Y \qquad (VII)$$

wherein $R_2$, $R_3$, $R_4$ and $R_5$ are as defined for formula I and Y is a removable group, for example a halogen atom, in particular a chlorine, bromine or iodine atom.

The process for the preparation of the thioanilines of formula V is conveniently carried out in the presence of an inorganic or organic base, for example an alkali metal hydroxide or carbonate, of an inert, preferably polar, solvent or diluent, and, if desired, of a catalyst, for example copper powder, a copper halide or copper carbonate, in the temperature range from 80° to 160° C. and under normal pressure. Examples of suitable solvents or diluents are: ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; or alcohols such as ethanol and methanol. Aprotic dipolar solvents such as dimethyl sulfoxide or dimethyl formamide are especially suitable. On account of the sensitivity of the anilines of formula VI to oxidation, it is advisable to carry out the reaction in an inert gas atmosphere.

The compounds of formulae II and V are novel and likewise constitute an object of the invention. On the other hand, the compounds of formulae III, IV, VI and VII are known or can be prepared by methods which are known per se.

Surprisingly, it has been found that the compounds of formula I of this invention are valuable pesticides while being well tolerated by warm-blooded animals and plants. The compounds of formula I are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the Larva and eggs. It is thus possible to control effectively in particular larvae and eggs of phytopathogenic insect pests and mites in crops of ornamentals and useful plants, for example in fruit and vegetable crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the chief pests are ectoparasites, such as mites and ticks and Diptera, for example Lucilia sericata.

The good pesticidal activity of the compounds of formula I corresponds to a mortality of at least 50-60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocabons, and Bacillus thuringiensis preparations.

The compounds of formula I are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (Active Ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures of substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The fulsonated benzimidazole derivatives preferably contain 2 sulfonic acid groups and one fatty radical containing 8 to 22 carbon atoms. Examples of alkylarylsulfonates are the sodium, calcium or triethanolamine salts of dodecylbenzenesulfonic acid, dibutylnapththalenesulfonic acid, or of a condensate of naththalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypopylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, ethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCuthcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE

Preparation 1.1 Intermediates 1.1.1. Thioanilines 1.1.1.1. 2,6-Diisopropyl-4(4', 5'-dichlorothiazol-2'-ylthio)aniline 26 g of 2,6-diisopropyl-4-mercaptoaniline and 22.4 g of powdered potassium carbonate are added to 100 ml of dry dimethyl sulfoxide and to this mixture are added, at room temperature, 23.5 g of 2,4,5-trichlorotriazine in 20 ml of dimethyl sulfoxide. The reaction solution is stirred for 24 hours at 90° C., then poured into 500 ml of ice-water. After repeated extraction with ether, the ethereal extracts are dried over sodium sulfate, the solvent is removed under vacuum, and the residue is chromatographed over silica gel with a 9:1 mixture of hexane/ethyl acetate as eluant. The title compound of formula (compound 1.1.1.1.)

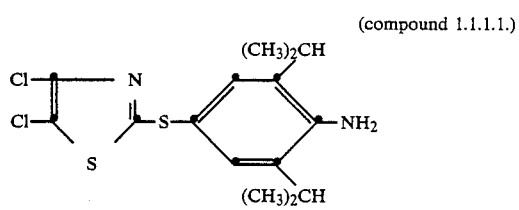

is obtained as a pale brown solid which melts at 100°–102° C.

The following compounds are prepared in analogous manner:

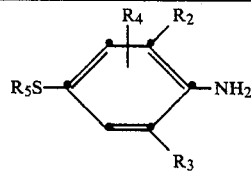

| Compound | R₂ | R₃ | R₄ | R₅* | R₇ | R₈ | R₉ | Physical data |
|---|---|---|---|---|---|---|---|---|
| 1.1.1.2. | CH(CH₃)₂ | CH(CH₃)₂ | H | Q₁' | Cl | Br | — | m.p. 120–123° C. |
| 1.1.1.3. | CH(CH₃)₂ | CH(CH₃)₂ | H | Q₄ | CH₃ | — | — | m.p. 112–114° C. |
| 1.1.1.4. | C₂H₅ | C₂H₅ | H | Q₄ | CH₃ | — | — | m.p. 139–141° C. |
| 1.1.1.5. | CH(CH₃)₂ | CH(CH₃)₂ | H | Q₁' | Cl | CH₃ | — | m.p. 94–96° C. |
| 1.1.1.6. | C₂H₅ | C₂H₅ | H | Q₁' | Cl | Cl | — | m/e = 332/334 |
| 1.1.1.7. | C₂H₅ | CH(CH₃)C₂H₅ | H | Q₄ | CH₃ | — | — | m.p. 53–55° C. |
| 1.1.1.8. | CH(CH₃)₂ | CH(CH₃)₂ | H | Q₄ | CH(CH₃)₂ | — | — | m/e = 335 |
| 1.1.1.9. | CH(CH₃)₂ | CH(CH₃)₂ | H | Q₇ | 6-Cl | — | — | m.p. 117–119° C. |
| 1.1.1.10. | C₂H₅ | CH(CH₃)₂ | H | Q₁' | Cl | Cl | — | m/e = 346/348 |
| 1.1.1.11. | CH(CH₃)₂ | CH(CH₃)₂ | H | Q₈ | H | H | — | m.p. 133–135° C. |
| 1.1.1.12. | CH(CH₃)₂ | CH(CH₃)₂ | H | Q₈ | 6-Cl | H | — | m.p. 108–110° C. |
| 1.1.1.13. | CH(CH₃)₂ | CH(CH₃)₂ | H | Q₈ | 4-Cl | H | — | m.p. 179.5–181.5° C. |
|  | CH₃ | CH₃ | H | Q₂ | CF₃ | — | CH(CH₃)₂ |  |
|  | CH(CH₃)₂ | CH(CH₃)₂ | H | Q₂ | CF₃ | — | CH(CH₃)₂ |  |
|  | CH(CH₃)₂ | CH(CH₃)₂ | H | Q₃ | CF₃ | — | — |  |
|  | cyclopentyl | CH(CH₃)₂ | H | Q₁' | Cl | Cl | — |  |

*Q₁'

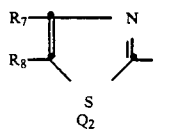

Q₂

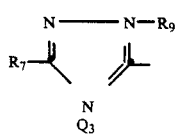

Q₃

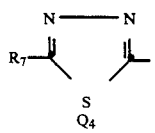

Q₄

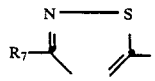

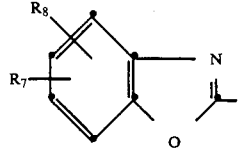

Q₇

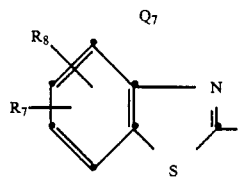

Q₈

1.1.2. Isothiocyanates 1.1.2.1. 2,6-Diisopropyl-4-(4',5'-dichlorothiazol-2'-ylthio)-phenylisothiocyanate 4.2 g of thiophosgene, 6 g of calcium carbonate and 70 ml of dichloromethane are stirred in 45 ml of water. With stirring, a solution of 10.8 g of 2,6-diisopropyl-4-(4',5'-dichlorothiazol-2'-ylthio)aniline in 20 ml of dichloromethane is added dropwise at room temperature to the above mixture. The reaction mixture is stirred for 2 hours under reflux, then cooled and filtered. The organic phase is separated from the filtrate and the aqueous phase is washed with dichloromethane. The combined organic phases are washed with water, dried over sodium sulfate, and finally the solvent is removed by distillation. The title compound of formula

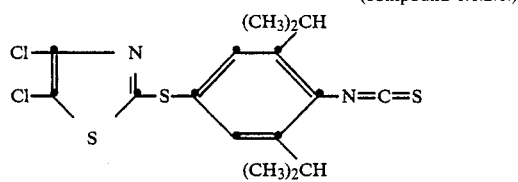

(compound 1.1.2.1.)

is obtained in the form of a yellow oil, which is used without further purification for the next reaction.

The following compounds are prepared in analogous manner:

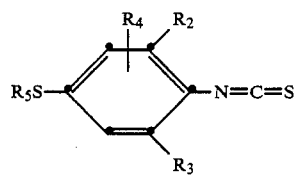

| Compound | $R_2$ | $R_3$ | $R_4$ | $R_5$* | $R_7$ | $R_8$ | $R_9$ | Physical data |
|---|---|---|---|---|---|---|---|---|
| 1.1.2.2. | $CH(CH_3)_2$ | $CH(CH_3)_2$ | H | $Q_1'$ | Cl | Br | — | brown solid |
| 1.1.2.3. | $CH(CH_3)_2$ | $CH(CH_3)_2$ | H | $Q_4$ | $CH_3$ | — | — | m.p. 92–93° C. |
| 1.1.2.4. | $C_2H_5$ | $C_2H_5$ | H | $Q_4$ | $CH_3$ | — | — | m.p. 35–37° C. |
| 1.1.2.5. | $CH(CH_3)_2$ | $CH(CH_3)_2$ | H | $Q_1'$ | Cl | $CH_3$ | — | m.p. 75–78° C. |
| 1.1.2.6. | $C_2H_5$ | $C_2H_5$ | H | $Q_1'$ | Cl | Cl | — | yellow solid |
| 1.1.2.7. | $C_2H_5$ | $CH(CH_3)C_2H_5$ | H | $Q_4$ | $CH_3$ | — | — | $n_D^{25}$: 1.658 |
| 1.1.2.8. | $CH(CH_3)_2$ | $CH(CH_3)_2$ | H | $Q_4$ | $CH(CH_3)_2$ | — | — | m.p. 30° C. |
| 1.1.2.9. | $CH(CH_3)_2$ | $CH(CH_3)_2$ | H | $Q_7$ | 6-Cl | — | — | m.p. 82–84° C. |
| 1.1.2.10. | $C_2H_5$ | $CH(CH_3)_2$ | H | $Q_1'$ | Cl | Cl | — | yellow solid |
| 1.1.2.11. | $CH(CH_3)_2$ | $CH(CH_3)_2$ | H | $Q_8$ | H | H | — | m.p. 122–124,5° C. |
| 1.1.2.12. | $CH(CH_3)_2$ | $CH(CH_3)_2$ | H | $Q_8$ | 6-Cl | H | — | m.p. 168–169° C. |
| 1.1.2.13. | $CH(CH_3)_2$ | $CH(CH_3)_2$ | H | $Q_8$ | 4-Cl | H | — | pale yellow solid |
| | $CH_3$ | $CH_3$ | H | $Q_2$ | $CF_3$ | — | $CH(CH_3)_2$ | |
| | $CH(CH_3)_2$ | $CH(CH_3)_2$ | H | $Q_2$ | $CF_3$ | — | $CH(CH_3)_2$ | |
| | $CH(CH_3)_2$ | $CH(CH_3)_2$ | H | $Q_3$ | $CF_3$ | — | — | |

-continued

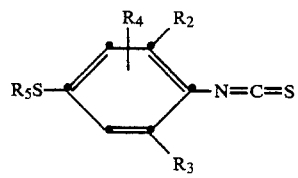

| Compound | $R_2$ | $R_3$ | $R_4$ | $R_5$* | $R_7$ | $R_8$ | $R_9$ | Physical data |
|---|---|---|---|---|---|---|---|---|
| | cyclopentyl | $CH(CH_3)_2$ | H | $Q_1'$ | Cl | Cl | — | |

*$Q_1'$

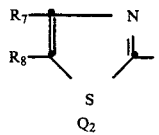

$Q_2$

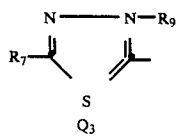

$Q_3$

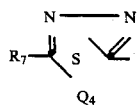

$Q_4$

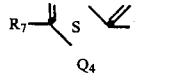

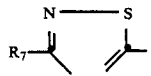

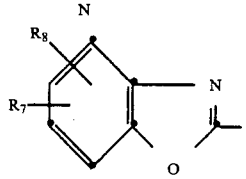

$Q_7$

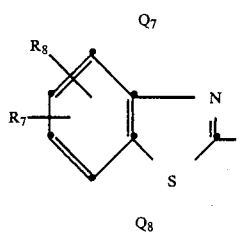

$Q_8$

1.2. Final products

1.2.1. Phenylthioureas 1.2.1.1. N-[2,6-Diisopropyl-4-(4', 5'-dichlorothiazol-2'-ylthio)phenyl]-N'-tert-butylthiourea 7.7 g of 2,6-diisopropyl-4-(4',5'-dichlorothiazol-2'-ylthio)phenylisothiocyanate and 3.0 g of tert-butylamine are diluted with 50 ml of tetrahydrofuran and the reaction mixture is warmed for 6 hours to 40°C. The reaction mixture is then poured into water and the precipitate is filtered and recrystallised from hexane/toluene. The title compound of formula

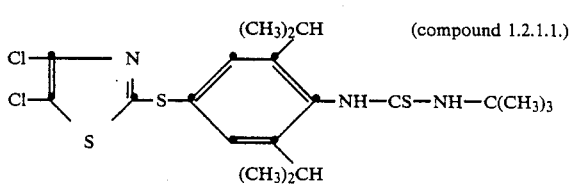 (compound 1.2.1.1.)

is obtained in the form of colourless crystals which melt at 153°–154° C.

The following compounds are prepared in analogous manner:

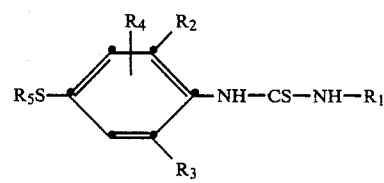

| Compound | $R_1$ | $R_2$ | $R_3$ | $R_4$ | $R_5$* | $R_7$ | $R_8$ | $R_9$ | m.p. °C. |
|---|---|---|---|---|---|---|---|---|---|
| 1.2.1.2. | $C(CH_3)_3$ | $CH(CH_3)_2$ | $CH(CH_3)_2$ | H | $Q_1'$ | Cl | Br | — | 172–173 |
| 1.2.1.3. | $C(CH_3)_3$ | $CH(CH_3)_2$ | $CH(CH_3)_2$ | H | $Q_4$ | $CH_3$ | — | — | 146–148 |
| 1.2.1.4. | $C(CH_3)_3$ | $C_2H_5$ | $C_2H_5$ | H | $Q_4$ | $CH_3$ | — | — | 108–110 |
| 1.2.1.5. | $CH(CH_3)_2$ | $C_2H_5$ | $C_2H_5$ | H | $Q_4$ | $CH_3$ | — | — | 142–144 |
| 1.2.1.6. | $CH(CH_3)C_2H_5$ | $C_2H_5$ | $C_2H_5$ | H | $Q_4$ | $CH_3$ | — | — | 97–99 |
| 1.2.1.7. | $C(CH_3)_3$ | $CH(CH_3)_2$ | $CH(CH_3)_2$ | H | $Q_1'$ | Cl | $CH_3$ | — | 160–162 |
| 1.2.1.8. | $CH(CH_3)_2$ | $CH(CH_3)_2$ | $CH(CH_3)_2$ | H | $Q_1'$ | Cl | $CH_3$ | — | 158–161 |
| 1.2.1.9. | cyclopentyl | $CH(CH_3)_2$ | $CH(CH_3)_2$ | H | $Q_1'$ | Cl | $CH_3$ | — | 163.5–166 |
| 1.2.1.10. | $C(CH_3)_3$ | $C_2H_5$ | $C_2H_5$ | H | $Q_1'$ | Cl | Cl | — | 135.5–139 |
| 1.2.1.11. | cyclopentyl | $C_2H_5$ | $C_2H_5$ | H | $Q_4$ | $CH_3$ | — | — | 148–150 |
| 1.2.1.12. | $CH(CH_3)_2$ | $CH(CH_3)_2$ | $CH(CH_3)_2$ | H | $Q_4$ | $CH_3$ | — | — | 118–119 |
| 1.2.1.13. | $CH(CH_3)C_2H_5$ | $CH(CH_3)_2$ | $CH(CH_3)_2$ | H | $Q_4$ | $CH_3$ | — | — | 118–119 |
| 1.2.1.14. | $C(CH_3)_2C_2H_5$ | $CH(CH_3)_2$ | $CH(CH_3)_2$ | H | $Q_4$ | $CH_3$ | — | — | 142–144 |
| 1.2.1.15. | cyclopentyl | $CH(CH_3)_2$ | $CH(CH_3)_2$ | H | $Q_4$ | $CH_3$ | — | — | 154–156 |
| 1.2.1.16. | $C(CH_3)_3$ | $C_2H_5$ | $CH(CH_3)C_2H_5$ | H | $Q_4$ | $CH_3$ | — | — | 112–114 |
| 1.2.1.17. | $CH(CH_3)_2$ | $C_2H_5$ | $CH(CH_3)C_2H_5$ | H | $Q_4$ | $CH_3$ | — | — | 78–80 |
| 1.2.1.18. | $C(CH_3)_3$ | $CH(CH_3)_2$ | $CH(CH_3)_2$ | H | $Q_4$ | $CH(CH_3)_2$ | — | — | 144–146 |
| 1.2.1.19. | $CH(CH_3)_2$ | $C_2H_5$ | $C_2H_5$ | H | $Q_1'$ | Cl | Cl | — | 146–147 |
| 1.2.1.20. | $C(CH_3)_3$ | $CH(CH_3)_2$ | $C_2H_5$ | H | $Q_1'$ | Cl | Cl | — | 132–138 |
| 1.2.1.21. | $CH(CH_3)_2$ | $CH(CH_3)_2$ | $C_2H_5$ | H | $Q_1'$ | Cl | Cl | — | 159–162 |
| 1.2.1.22. | $C(CH_3)_3$ | $CH(CH_3)_2$ | $CH(CH_3)_2$ | H | $Q_7$ | 6-Cl | H | — | 134 |
| 1.2.1.23. | $C(CH_3)_3$ | $CH(CH_3)_2$ | $CH(CH_3)_2$ | H | $Q_8$ | H | H | — | 142–144 |
| 1.2.1.24. | $CH(CH_3)_2$ | $CH(CH_3)_2$ | $CH(CH_3)_2$ | H | $Q_8$ | H | H | — | 178–181 |
| 1.2.1.25. | $C(CH_3)_3$ | $CH(CH_3)_2$ | $CH(CH_3)_2$ | H | $Q_8$ | 4-Cl | H | — | 153.5–155.5 |
| 1.2.1.26. | $CH(CH_3)_2$ | $CH(CH_3)_2$ | $CH(CH_3)_2$ | H | $Q_8$ | 6-Cl | H | — | 181–183.5 |
| 1.2.1.27. | $C(CH_3)_3$ | $CH(CH_3)_2$ | $CH(CH_3)_2$ | H | $Q_8$ | 6-Cl | H | — | 152–153 |
|  | $C(CH_3)_3$ | $CH_3$ | $CH_3$ | H | $Q_2$ | $CF_3$ | — | $CH(CH_3)_2$ |  |
|  | $C(CH_3)_3$ | $CH(CH_3)_2$ | $CH(CH_3)_2$ | H | $Q_2$ | $CF_3$ | — | $CH(CH_3)_2$ |  |
|  | $C(CH_3)_3$ | $CH(CH_3)_2$ | $CH(CH_3)_2$ | H | $Q_3$ | $CF_3$ | — | — |  |
|  | cyclopentyl | $CH(CH_3)_2$ | $CH(CH_3)_2$ | H | $Q_1'$ | Cl | Cl | — |  |
|  | cyclopentyl | $CH(CH_3)_2$ | $CH(CH_3)_2$ | H | $Q_1'$ | $CH_3$ | — | — |  |

-continued

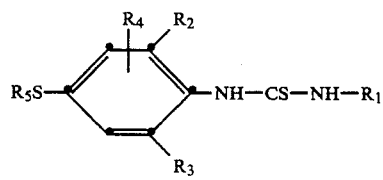

| Compound | $R_1$ | $R_2$ | $R_3$ | $R_4$ | $R_5$* | $R_7$ | $R_8$ | $R_9$ | m.p. °C. |
|---|---|---|---|---|---|---|---|---|---|
| | $C(CH_3)_3$ | cyclopentyl | $CH(CH_3)_2$ | H | $Q_1'$ | Cl | Cl | — | |

*$Q_1'$

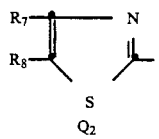

$Q_2$

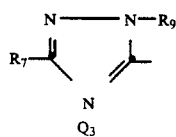

$Q_3$

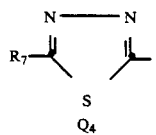

$Q_4$

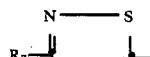

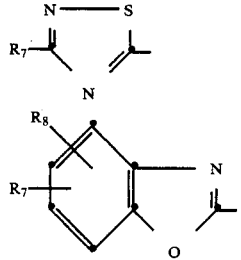

$Q_7$

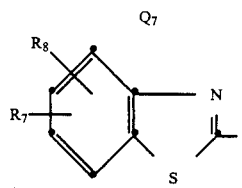

$Q_8$

1.2.2. Phenylisothioureas 1.2.2.1. N-[2,6-Diisopropyl-4-(4',5'-dichlorothiazol-2'-ylthio)phenyl]-N'-(tert-butyl)-S-methylisothiourea 1.6 g of methyl iodide are added at room temperature to 3.6 g of N-[2,6-diisopropyl-4-(4',5'-dichlorothiazol-2'-ylthi)phenyl]-N'-tert-butylthiourea in 40 ml of ethanol and the mixture is heated for 6 hours to 50° C. The reaction solution is then concentrated by evaporation and the residue is taken up on methylene chloride and the solution is washed twice with dilute sodium carbonate solution. The organic phase is dried over sodium sulfate and the solvent is removed by evaporation, affording the title compound of formula

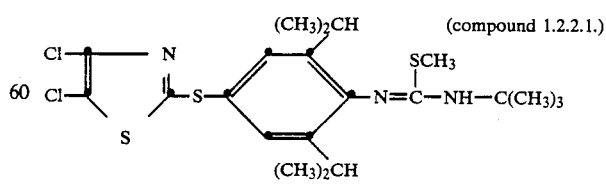

(compound 1.2.2.1.)

in the form of a colourless crystalline powder with a melting point of 116°–117° C.

The following compounds are prepared in analogous manner:

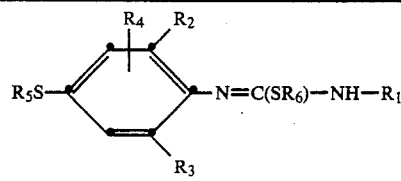

| Compound | R₁ | R₂ | R₃ | R₄ | R₅* | R₆ | R₇ | R₈ | R₉ | Physical data |
|---|---|---|---|---|---|---|---|---|---|---|
| 1.2.2.2. | C(CH₃)₃ | CH(CH₃)₂ | CH(CH₃)₂ | H | Q₁' | CH₃ | Cl | Br | — | m.p. 118.5–119.5° C. |
| 1.2.2.3. | C(CH₃)₃ | CH(CH₃)₂ | CH(CH₃)₂ | H | Q₄ | CH₃ | CH₃ | — | — | m.p. 114–116° C. |
| 1.2.2.4. | C(CH₃)₃ | C₂H₅ | C₂H₅ | H | Q₄ | C₂H₅ | CH₃ | — | — | m.p. 82–84° C. |
| 1.2.2.5. | CH(CH₃)₂ | C₂H₅ | C₂H₅ | H | Q₄ | CH₃ | CH₃ | — | — | $n_D^{40}$: 1.5984 |
| 1.2.2.6. | CH(CH₃)C₂H₅ | C₂H₅ | C₂H₅ | H | Q₄ | CH₃ | CH₃ | — | — | $n_D^{25}$: 1.5934 |
| 1.2.2.7. | C(CH₃)₃ | CH(CH₃)₂ | CH(CH₃)₂ | H | Q₁' | CH₃ | Cl | CH₃ | — | m.p. 95–98° C. |
| 1.2.2.8. | CH(CH₃)₂ | CH(CH₃)₂ | CH(CH₃)₂ | H | Q₁' | CH₃ | Cl | CH₃ | — | m.p. 93–95° C. |
| 1.2.2.9. | cyclopentyl | CH(CH₃)₂ | CH(CH₃)₂ | H | Q₁' | CH₃ | Cl | CH₃ | — | m.p. 101.5–102.5° C. |
| 1.2.2.10. | C(CH₃)₃ | C₂H₅ | C₂H₅ | H | Q₁' | CH₃ | Cl | Cl | — | m.p. 61.5–63.5° C. |
| 1.2.2.11. | cyclopentyl | C₂H₅ | C₂H₅ | H | Q₄ | CH₃ | CH₃ | — | — | $n_D^{40}$: 1.5995 |
| 1.2.2.12. | CH(CH₃)C₂H₅ | CH(CH₃)₂ | CH(CH₃)₂ | H | Q₄ | CH₃ | CH₃ | — | — | $n_D^{40}$: 1.5796 |
| 1.2.2.13. | C(CH₃)₂C₂H₅ | CH(CH₃)₂ | CH(CH₃)₂ | H | Q₄ | CH₃ | CH₃ | — | — | m.p. 96–98° C. |
| 1.2.2.14. | CH(CH₃)₂ | C₂H₅ | CH(CH₃)C₂H₅ | H | Q₄ | CH₃ | CH₃ | — | — | $n_D^{40}$: 1.5875 |
| 1.2.2.15. | cyclopentyl | CH(CH₃)₂ | CH(CH₃)₂ | H | Q₄ | CH₃ | CH₃ | — | — | m.p. 114–116° C. |
| 1.2.2.16. | C(CH₃)₃ | CH(CH₃)₂ | CH(CH₃)₂ | H | Q₄ | CH₃ | CH(CH₃)₂ | — | — | m.p. 91–93° C. |
| 1.2.2.17. | CH(CH₃)₂ | C₂H₅ | C₂H₅ | H | Q₁' | CH₃ | Cl | Cl | — | m.p. 78–80° C. |
| 1.2.2.18. | C(CH₃)₃ | CH(CH₃)₂ | C₂H₅ | H | Q₁' | CH₃ | Cl | Cl | — | $n_D^{39}$: 1.6037 |
| 1.2.2.19. | CH(CH₃)₂ | CH(CH₃)₂ | C₂H₅ | H | Q₁' | CH₃ | Cl | Cl | — | $n_D^{39}$: 1.5991 |
| 1.2.2.20. | C(CH₃)₃ | CH(CH₃)₂ | CH(CH₃)₂ | H | Q₈ | CH₃ | H | H | — | m.p. 166.5–168° C. |
| 1.2.2.21. | CH(CH₃)₂ | CH(CH₃)₂ | CH(CH₃)₂ | H | Q₈ | CH₃ | H | H | — | m.p. 108–111° C. |
| 1.2.2.22. | C(CH₃)₃ | CH(CH₃)₂ | CH(CH₃)₂ | H | Q₈ | CH₃ | 4-Cl | H | — | m.p. 175–176° C. |
| 1.2.2.23. | CH(CH₃)₂ | CH(CH₃)₂ | CH(CH₃)₂ | H | Q₈ | CH₃ | 6-Cl | H | — | m.p. 105.5–107.5° C. |
| 1.2.2.24. | C(CH₃)₃ | CH(CH₃)₂ | CH(CH₃)₂ | H | Q₈ | CH₃ | 6-Cl | H | — | m.p. 168–172° C. |
| 1.2.2.25. | CH(CH₃)₂ | CH(CH₃)₂ | CH(CH₃)₂ | H | Q₄ | CH₃ | CH₃ | — | — | $n_D^{40}$: 1.5847 |
|  | C(CH₃)₃ | CH₃ | CH₃ | H | Q₂ | CH₃ | CF₃ | — | CH(CH₃)₂ |  |
|  | C(CH₃)₃ | CH(CH₃)₂ | CH(CH₃)₂ | H | Q₂ | CH₃ | CF₃ | — | CH(CH₃)₂ |  |
|  | CH(CH₃)₂ | CH(CH₃)₂ | CH(CH₃)₂ | H | Q₄ | CH₃ | CH₃ | — | — |  |
|  | C(CH₃)₃ | CH(CH₃)₂ | CH(CH₃)₂ | H | Q₃ | CH₃ | CF₃ | — | — |  |
|  | cyclopentyl | CH(CH₃)₂ | CH(CH₃)₂ | H | Q₁' | CH₃ | Cl | Cl | — |  |
|  | cyclopentyl | CH(CH₃)₂ | CH(CH₃)₂ | H | Q₁' | CH₃ | CH₃ | — | — |  |
|  | C(CH₃)₃ | cyclopentyl | CH(CH₃)₂ | H | Q₁' | CH₃ | Cl | Cl | — |  |
|  | C(CH₃)₃ | C₂H₅ | CH(CH₃)C₂H₅ | H | Q₄ | CH₃ | CH₃ | — | — |  |

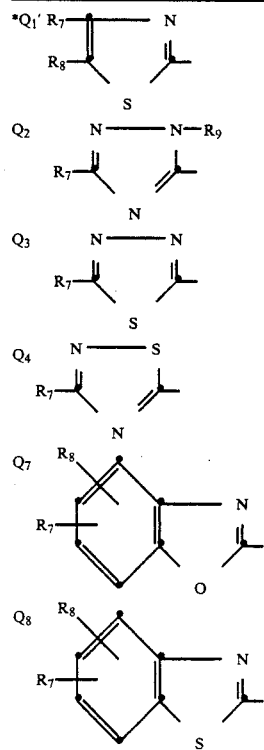

1.2.3. Phenylisothiourea salts 1.2.3.1. N-[2,6-Diisopropyl-4(4'-chloro-5'-methyl-thiazol-2'-ylthio)-phenyl]-N'-isopropyl-S-methylisothiourea hydroiodide 5 g of N-[2,6-diisopropyl-4-(4',5'-chloro-5'-methyl-thiazol-2'-ylthio)-phenyl]-N'-isopropyl-S-methylisothiourea are dissolved in 20 ml of absolute diethyl ether and 1 g of hydriodic acid is then added to this solution. The reaction solution is stirred for 3 hours at room temperature. The precipitate is filtered with suction and dried, affording the title compound of formula

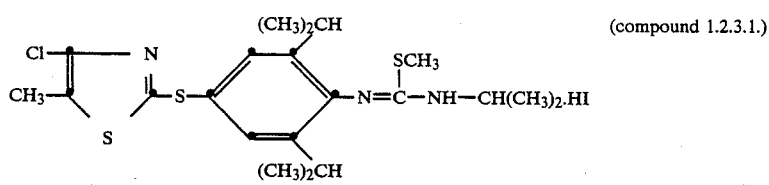

(compound 1.2.3.1.)

in the form of a colourless crystalline powder with a melting point of 180°–183° C.

The following compounds are prepared in analogous manner:

chloro-1-methylpyridinium iodide are added to 40 ml of dry acetonitrile. Then 2.3 g of triethylamine in 50 ml of acetonitrile are added dropwise at room temperature and the mixture is stirred for 3 hours under reflux. The solvent is removed under vacuum and the residue is taken up in hexane and the solution is filtered. The filtrate is washed three times with water, dried over sodium sulfate and the solvent is removed under vacuum, affording the title compound of formula (compound 1.2.4.1.)

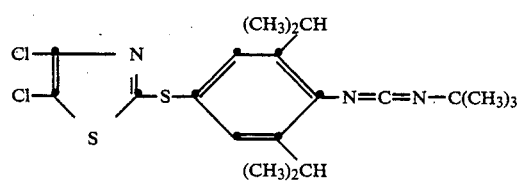

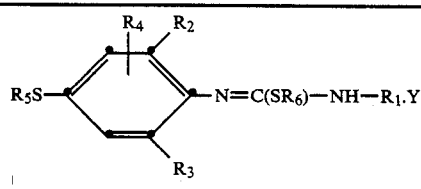

| Compound | R₁ | R₂ | R₃ | R₄ | R₅* | R₆ | R₇ | R₈ | R₉ | Y | m.p. °C. |
|---|---|---|---|---|---|---|---|---|---|---|---|
| 1.2.3.2. | Cyclopentyl | CH(CH₃)₂ | CH(CH₃)₂ | H | Q₁' | CH₃ | Cl | CH₃ | — | HI | 167–170 |
| 1.2.3.3. | CH(CH₃)₂ | CH(CH₃)₂ | C₂H₅ | H | Q₁' | CH₃ | Cl | Cl | — | HI | 152–159 |
| 1.2.3.4. | C(CH₃)₃ | CH(CH₃)₂ | CH(CH₃)₂ | H | Q₈ | CH₃ | H | H | — | HI | 157–160 |
| 1.2.3.5. | CH(CH₃)₂ | CH(CH₃)₂ | CH(CH₃)₂ | H | Q₈ | CH₃ | H | H | — | HI | 159–163 |
| 1.2.3.6. | CH(CH₃)₂ | CH(CH₃)₂ | CH(CH₃)₂ | H | Q₈ | CH₃ | 6-Cl | H | — | HI | 174–180 |

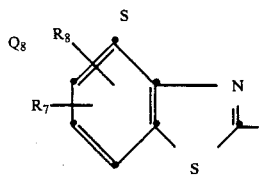

1.2.4. Phenylcarbodiimides 1.2.4.1. N-[2,6-Diisopropyl-4-(4',5'-dichlorothiazol-2'-ylthio)phenyl]-N'-tert-butylcarbodiimide 4.2 g of N-[2,6-diisopropyl-4-(4',5'-dichlorothiazol-2'-ylthio)phenyl]-N'-tert-butylthiourea and 2.9 g of 2- in the form of a colourless crystalline powder with a melting point of 60.5°–61.5° C.

The following compounds are prepared in analogous manner:

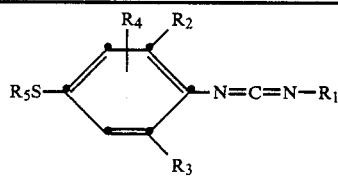

| Compound | R₁ | R₂ | R₃ | R₄ | R₅* | R₇ | R₈ | R₉ | Physical data |
|---|---|---|---|---|---|---|---|---|---|
| 1.2.4.2. | C(CH₃)₃ | CH(CH₃)₂ | CH(CH₃)₂ | H | Q₁' | Cl | Br | — | m.p. 60.5–61.5° C. |

-continued

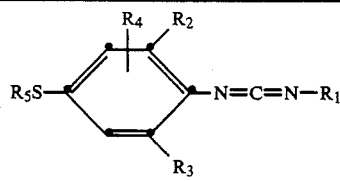

| Compound | R₁ | R₂ | R₃ | R₄ | R₅* | R₇ | R₈ | R₉ | Physical data |
|---|---|---|---|---|---|---|---|---|---|
| 1.2.4.3. | C(CH₃)₃ | CH(CH₃)₂ | CH(CH₃)₂ | H | Q₄ | CH₃ | — | — | $n_D^{40}$: 1.5730 |
| 1.2.4.4. | C(CH₃)₃ | C₂H₅ | C₂H₅ | H | Q₄ | CH₃ | — | — | $n_D^{40}$: 1.5897 |
| 1.2.4.5. | CH(CH₃)₂ | C₂H₅ | C₂H₅ | H | Q₄ | CH₃ | — | — | $n_D^{40}$: 1.5926 |
| 1.2.4.6. | C(CH₃)₃ | CH(CH₃)₂ | CH(CH₃)₂ | H | Q₁' | Cl | CH₃ | — | m.p. 82–83.5° C. |
| 1.2.4.7. | CH(CH₃)₂ | CH(CH₃)₂ | CH(CH₃)₂ | H | Q₁' | Cl | CH₃ | — | m.p. 69–71° C. |
| 1.2.4.8. | cyclopentyl | CH(CH₃)₂ | CH(CH₃)₂ | H | Q₁' | Cl | CH₃ | — | m.p. 69–71° C. |
| 1.2.4.9. | C(CH₃)₃ | C₂H₅ | C₂H₅ | H | Q₁' | Cl | Cl | — | m.p. 62–65° C. |
| 1.2.4.10. | CH(CH₃)C₂H₅ | C₂H₅ | C₂H₅ | H | Q₄ | CH₃ | — | — | $n_D^{25}$: 1.5934 |
| 1.2.4.11. | cyclopentyl | C₂H₅ | C₂H₅ | H | Q₄ | CH₃ | — | — | $n_D^{25}$: 1.6095 |
| 1.2.4.12. | CH(CH₃)₂ | CH(CH₃)₂ | CH(CH₃)₂ | H | Q₄ | CH₃ | — | — | $n_D^{25}$: 1.5860 |
| 1.2.4.13. | CH(CH₃)C₂H₅ | CH(CH₃)₂ | CH(CH₃)₂ | H | Q₄ | CH₃ | — | — | $n_D^{25}$: 1.5820 |
| 1.2.4.14. | C(CH₃)₂C₂H₅ | CH(CH₃)₂ | CH(CH₃)₂ | H | Q₄ | CH₃ | — | — | $n_D^{25}$: 1.5765 |
| 1.2.4.15. | C(CH₃)₃ | C₂H₅ | CH(CH₃)C₂H₅ | H | Q₄ | CH₃ | — | — | $n_D^{25}$: 1.5793 |
| 1.2.4.16. | CH(CH₃)₂ | C₂H₅ | CH(CH₃)C₂H₅ | H | Q₄ | CH₃ | — | — | $n_D^{25}$: 1.5865 |
| 1.2.4.17. | cyclopentyl | CH(CH₃)₂ | CH(CH₃)₂ | H | Q₄ | CH₃ | — | — | $n_D^{25}$: 1.5955 |
| 1.2.4.18. | C(CH₃)₃ | CH(CH₃)₂ | CH(CH₃)₂ | H | Q₄ | CH(CH₃)₂ | — | — | m.p. 50–52° C. |
| 1.2.3.19. | CH(CH₃)₂ | C₂H₅ | C₂H₅ | H | Q₁' | Cl | Cl | — | $n_D^{24}$: 1.6183 |
| 1.2.4.20. | C(CH₃)₃ | CH(CH₃)₂ | C₂H₅ | H | Q₁' | Cl | Cl | — | $n_D^{24}$: 1.6040 |
| 1.2.4.21. | CH(CH₃)₂ | CH(CH₃)₂ | C₂H₅ | H | Q₁' | Cl | Cl | — | $n_D^{24}$: 1.6121 |
| 1.2.4.22. | C(CH₃)₃ | CH(CH₃)₂ | CH(CH₃)₂ | H | Q₇ | 6-Cl | H | — | $n_D^{25}$: 1.5992 |
| 1.2.4.23. | C(CH₃)₃ | CH(CH₃)₂ | CH(CH₃)₂ | H | Q₈ | H | H | — | m.p. 80.5–82° C. |
| 1.2.4.24. | CH(CH₃)₂ | CH(CH₃)₂ | CH(CH₃)₂ | H | Q₈ | H | H | — | m.p. 62–65.5° C. |
| 1.2.4.25. | C(CH₃)₃ | CH(CH₃)₂ | CH(CH₃)₂ | H | Q₈ | 4-Cl | H | — | m.p. 133–134° C. |
| 1.2.4.26. | CH(CH₃)₂ | CH(CH₃)₂ | CH(CH₃)₂ | H | Q₈ | 6-Cl | H | — | m.p. 83–86° C. |
| 1.2.4.27. | C(CH₃)₃ | CH(CH₃)₂ | CH(CH₃)₂ | H | Q₈ | 6-Cl | H | — | m.p. 104–107.5° C. |
|  | C(CH₃)₃ | CH₃ | CH₃ | H | Q₂ | CF₃ | — | CH(CH₃)₂ |  |
|  | C(CH₃)₃ | CH(CH₃)₂ | CH(CH₃)₂ | H | Q₂ | CF₃ | — | CH(CH₃)₂ |  |
|  | C(CH₃)₃ | CH(CH₃)₂ | CH(CH₃)₂ | H | Q₃ | CF₃ | — | — |  |
|  | cyclopentyl | CH(CH₃)₂ | CH(CH₃)₂ | H | Q₁' | Cl | Cl | — |  |
|  | cylcopentyl | CH(CH₃)₂ | CH(CH₃)₂ | H | Q₁' | CH₃ | — | — |  |
|  | C(CH₃)₃ | cyclopentyl | CH(CH₃)₂ | H | Q₁' | Cl | Cl | — |  |

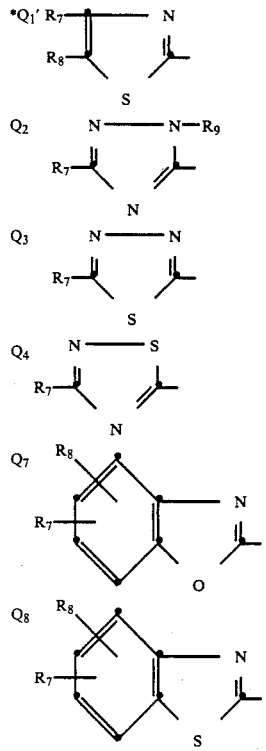

EXAMPLE 2

Formulations of compounds of formula I according to Preparatory Examples 1.2

(throughout, percentages are by weight)

| 2.1. Emulsifiable concentrates | (a) | (b) |
|---|---|---|
| a compound according to Preparatory Examples 1.2. | 10% | 25% |
| calcium dodecylbenzenesulfonate | — | 5% |
| castor oil polyethylene glycol ether (36 mol of ethylene oxide) | 25% | 5% |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

| 2.2. Solutions | (a) | (b) |
|---|---|---|
| a compound according to Preparatory Examples 1.2. | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160–190° C.) | — | 74% |

These solutions are suitable for applications in the form of microdrops.

| 2.3. Granulates | (a) | (b) |
|---|---|---|
| a compound according to Preparatory Examples 1.2. | 5% | 10% |
| kaolin | 94% | — |
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| 2.4. Extruder granulate | |
|---|---|
| a compound according to Preparatory Examples 1.2. | 10% |
| sodium lignosulfonate | 2% |
| carboxymethylcellulose | 1% |
| kaolin | 87% |

The active ingredient or ingredients is or are mixed and ground with the adjuvants, and the mixture is subsequently moistened with water. The mixture is extruded and then dried in a stream of air.

| 2.5. Coated granulate | |
|---|---|
| a compound according to Preparatory Examples 1.2. | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| a compound according to Preparatory Examples 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and, optionally, grinding the mixture in a suitable mill.

| 2.7. Wettable powders | (a) | (b) | (c) |
|---|---|---|---|
| a compound according to Preparatory Examples 1.2. | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Examples 1.2. | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Tests

3.1. Action against *Musca domestica*

A sugar lump is moistened with a solution of the test compound in an amount sufficient to give a concentration of 500 ppm of active ingredient in the dried lump. The treated sugar lump is placed in a dish together with a wet cotton wool swab and covered with a glass beaker. Ten adult one-week-old and OP-resistant flies are then placed beneath the beaker and kept at 25° C. and 50% humidity. The insecticidal activity is evaluated by determining mortality after 24 hours.

Compounds of Examples 1.2. exhibit good activity in this test.

3.2. Contact action against *Aphis craccivora*

Before the start of the test, 4- to 5-day old pea seedlings (Pisum sativum) grown in pots are each populated with about 200 insects of the species *Aphis craccivora*. The treated plants are sprayed direct to drip point 24 hours later with an aqueous formulation containing 400 ppm of the test compound. Two plants are used for each test compound at its given concentration. A mortality count is made after 3 and 5 days respectively. The test is carried out at ca. 21° C. and at a relative humidity of about 55%.

Compounds of Examples 1.2. exhibit good activity in this test against *Aphis cracivora*.

3.3. Action against ectoparasiticidal ticks

Ten Boophilus microplus females which are freshly replete with blood are affixed in a row in the dorsal position to a PVC plate and covered with a cotton wool swab. The swab is then impregnated with 10 ml of an aqueous solution of the test compound. One hour later the cotton wool swab is removed and the tricks are dried overnight at 24° C. After drying, the ticks are kept for 4 weeks at 28° C. and 80% relative humidity until oviposition is complete and the larvae have started to hatch.

Each test compound is applied in a concentration of 500 ppm. Acaricidal activity takes the form of either mortality or sterility of the female or of blockage of embryogenesis in the egg deposit or inhibition of hatching. All compounds are tested against two strains of tick, viz. the OP-resistant BIARRA strain and the amidine-resistant ULAM strain.

Compounds of Examples 1.2. exhibit good activity in this test.

3.4. Action against soil insects (*Diabrotica balteata*)

350 ml of soil (consisting of 95 vol. % of sand and 5 vol. % of peat) are mixed with 150 ml of an aqueous emulsion formulation which contains the test compound in a concentration of 400 ppm. Plastic beakers with a diameter of about 10 cm at the top are then partly filled with the treated soil. Ten $L_3$-larvae of *Diabrotica balteata* are put into each beaker, then 4 maize seedlings are planted and the beaker is filled up with soil. The beakers are sealed with plastic sheeting and kept at about 24° C. and ca. 50% relative humidity. Six days later the soil in the beakers is sieved and a mortality count of the remaining larvae is made.

Compounds of Examples 1.2. exhibit good activity in this test.

3.5. Stomach toxicant action against *Spodoptera littoralis* larvae $L_1$

Cotton plants in the cotyledon stage are sprayed with an aqueous emulsion (obtained from a 10% emulsifiable concentrate) containing 400 ppm of the test compound. After the spray coating has dried, each cotton plant is populated with *spodoptera littoralis* larvae in the $L_1$-stage. The test is carried out at 26° C. and ca. 50% relative humidity. After 2 and 3 days a morality count is made and, after 5 days, the larvae are also examined for inhibition of development and moulting.

Compounds of Examples 1.2. exhibit good activity in this test.

3.6. Stomach poison action against *Spodoptera littoralis* and *Heliothis virescens* larvae ($L_3$)

Potted soybean plants (pot size: 10 cm diameter) in the 4-leaf stage are sprayed with aqueous emulsions which contain the test compound in a concentration of 400 ppm.

After 2 days, each treated soybean plant is populated with 10 larvae of *spodoptera littoralis* and *Heliothis verescens* in the $L_3$-stage. The test is carried out at 26° C. and ca. 60% relative humidity in dim light. After 2 and 5 days evaluation is made to determine the percentage mortality of the larvae.

Compounds of Examples 1.2. effect 80–100% kill.

3.7. Insecticidal stomach poison action against *Plutella xylostella* larvae ($L_2$)

Potted Chinese cabbage plants (pot size: 10 cm diameter) in the 4-leaf stage are sprayed with aqueous emulsions which contain the test compound in a concentration of 400 ppm.

After 2 days, each treated Chinese cabbage plant is populated with 10 *Plutella xylostella* larvae in the $L_2$-stage. The test is carried out at 26° C. and ca. 60% relative humidity in dim light. After 2 and 5 days evaluation is made to determine the percentage mortality of the larvae.

Compounds of Examples 1.2. effect 80–100% kill.

3.8. Contact action against *Nilaparvata lugens* (nymphs)

The test is carried out with growing plants. For this purpose 4 rice plants (ca. 20 days old), about 15 cm in height, are planted into each of a number of pots (diameter 5.5 cm). The plants in each pot are sprayed on a rotary table with 40 ml of an acetonic solution containing 400 ppm of the respective test compound. After the spray coating has dried, each plant is populated with 20 nymphs of the test organisms in the second or third stage. To prevent the cicadas from escaping, a glass cylinder is slipped over each of the plants and sealed with a gauze top. The nymphs are kept for 6 days on the treated plant, which has to be watered again at least once. The test is carried out at about 23° C. and 55% relative humidity and the plants are exposed to light for 16 hours.

Compounds of Examples 1.2. exhibit good activity in this test.

3.9. Systemic action against *Nilaparvata lugens*

Rice plants which are about 10 days old and about 10 cm high are put into a plastic beaker which contains 20 ml of an aqueous emulsion formulation of the test compound in a concentration of 100 ppm and which is sealed with a perforated plastic lid. The root of each rice plant is pushed through a hole in the plastic lid into the aqueous test formulation. The perforation is sealed with cottonwool in order to fix the plant and to protect the test formulation from contact with the gas phase. The rice plant is then populated with 20 nymphs of *Nilaparvata lugens* in the $N_2$–$N_3$ stage and covered with a plastic cylinder. The test is carried out at 26° C. and ca. 60% relative humidity and the plant is exposed to light for 16 hours. A mortality count is made 2 and 5 days later, using untreated controls for comparison purposes, thereby establishing whether the test compound absorbed through the root kills the test organisms on the upper parts of the plant.

Compounds of Examples 1.2. effect 80–100% kill of *Nilaparvata lugens* in this test.

3.10. Action plant-destructive acarina: *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of Tetranychus urticae ((OP-sensitive) or *Tetranychus cin-*

*nabarinus* (OP-tolerant). The tolerance refers to the tolerance to diazinone. The treated infested plants are sprayed to drip point with an emulsified test solution containing the respective test compound in a concentration of 400 ppm. A count of the number of living and dead imagines and larvae (all mobile stages) is made under a stereoscopic microscope after 24 hours and again after 7 days and again after 7 days. One plant is used for each test species. During the test run, the plants are kept in greenhouse compartments at 25° C.

In this test, compounds of Examples 1.2. exhibit good activity against *Tetranychus urticae* and *Tetranychus connabarinus*.

3.11. Ovicidal action against *Tetranychus urticae* (OP-resistant)

Potted Phaseolus vulgaris plants in the primary leaf stage are each populated twice with 30 females of *Tetranychus urticae*. After oviposition for 24 hours, the females are removed from the plants with a suction pump (water jet pump), so that only the egg deposits on the plants remain. The egg-infested plants are then sprayed to drip point with an aqueous emulsion containing 400 ppm of the test compound and kept for 5 days at 25° C. and about 50% relative humidity. After this time a count is made to determine the percentage mortality of the eggs and of hatched out larvae.

Compounds of Examples 1.2. exhibit good activity in this test.

3.12. Miticidal leaf penetration action against *Tetranychus cinnabarinus*

Potted dwarf bean plants in the primary leaf stage infested with Tetranychus cinnabarinus are used for the test. The plants are populated with the mites one day before the application of the test compound.

The surface of the leaves of the plants infected with the mites are sprayed with an emulsion formulation containing 400 ppm of the test compound. After the spray coating has dried, a ribbon of viscous glue (caterpillar glue) is applied to the edge of the surface of each of a number of infested leaves so as to prevent the mites from migrating from the underside to the surface of the leaf.

The treated plants are then kept in a greenhouse at a temperature of 25°-27° C. and a relative humidity of ca. 50%. Six days after application the plants are examined to ascertain whether a tranlaminar effect has occurred, i.e. penetration of the test compound from the surface to the underside of the leaf, by determining the percentage mortality of the eggs and larval as well as adult stages.

Compounds of Examples 1.2. exhibit good activity in the test.

3.13. Action against *Panonychus ulmi* (OP and carbamate resistant)

Potted apple seedlings with about 20 to 30 leaves are each populated with 60 adult females of *Panonychus ulmi*. The infested plants are sprayed after 7 days to drip point with an aqueous emulsion containing 400 ppm of the test compounds. The treated plants are then stood in a greenhouse for a further 14 days at 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

Compounds of Examples 1.2. exhibit good activity in this test.

3.14. Action against parasitic mites in animals

Batches consisting of about 50 mites in different stages (larvae, nymphs and imagines) are taken from hens infested with *Dermanyssus gallinae*. The batches are each treated with an aqueous emulsion, suspension or solution containing 800 ppm of the test compound by pouring the liquid formulation of the test compound on to the mites present in a test tube. The liquid formulation is then absorbed by a cotton wool plug. The treated mites remain in the test tube for 72 hours, after which time the percentage mortality of the treated mites is determined in comparison with untreated controls.

Compounds of Examples 1.2. exhibit good activity in this test.

3.15. Action against ticks: inhibition of oviposition

Adult females of the cattle tick *Boophilus microplus* which are replete with blood are used as test organisms. 10 ticks of an OP-sensitive strain (e.g. Biarra strain) and 10 ticks of a normally sensitive strain (e.g. Yeerongpilly strain) are treated. The ticks are affixed to plates to which double-sided adhesive tape has been applied and are then either wetted with aqueous emulsions or solutions containing 800 ppm of the test compound or are brought into contact with cotton wool which has been impregnated with these liquids. The ticks are subsequently kept in a climatic chamber under constant conditions. Evaluation is made after 3 weeks. The percentage inhibition of the deposit of fertile eggs is determined in comparison with untreated controls.

Compounds of Examples 1.2. exhibit good activity in this test.

What is claimed is:

1. A compound of formula I

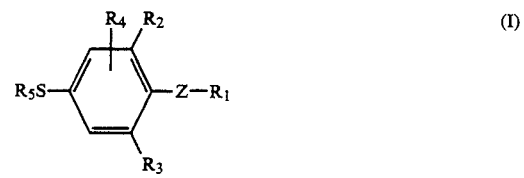

wherein $R_1$ is $C_1$–$C_7$alkyl which is substituted by one or more halogen atoms and/or $C_1$–$C_5$alkoxy groups; $C_5$–$C_6$cycloalkyl, $C_3$–$C_5$cycloalkyl-$C_1$–$C_3$alkyl or di($C_3$–$C_5$)cycloalkyl-$C_1$–$C_3$alkyl; $R_2$ is $C_1$–$C_4$alkyl or $C_5$–$C_6$cycloalkyl; $R_3$ is $C_1$–$C_4$alkyl; $R_4$ is hydrogen; $R_5$ is

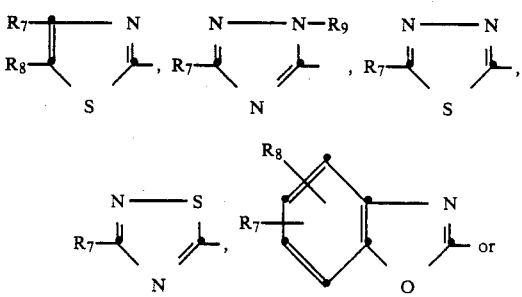

-continued

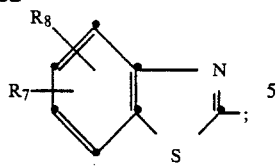

wherein $R_7$ and $R_8$ are each hydrogen, chlorine, bromine, $C_1$-$C_4$alkyl or $C_1$-$C_4$haloalkyl, and $R_9$ is $C_1$-$C_5$alkyl; Z is —NH—CS—NH—, —N=C(SR$_6$)—NH— or —N=C=N—; and $R_6$ is $C_1$-$C_5$alkyl.

2. A compound of formula I according to claim 1, wherein $R_1$ is $C_3$-$C_5$alkyl or $C_5$-$C_6$cycloalkyl; $R_2$ and $R_3$ are each $C_1$-$C_4$alkyl; $R_4$ is hydrogen; $R_5$ is

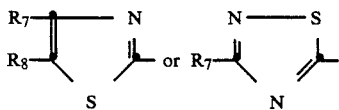

wherein $R_7$ and $R_8$ are each chlorine, bromine or methyl; and Z is —NH—CS—NH—.

3. A compound of formula I according to claim 1, wherein $R_1$ is $C_3$-$C_5$alkyl or $C_5$-$C_6$cycloalkyl; $R_2$ and $R_3$ are each $C_1$-$C_4$alkyl; $R_4$ is hydrogen; $R_5$ is

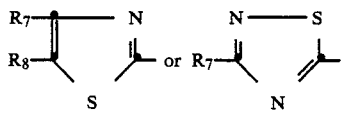

wherein $R_7$ and $R_8$ are each chlorine, bromine or methyl; Z is —N=C(SR$_6$)—NH—; and $R_6$ is methyl or ethyl.

4. A compound of formula I according to claim 1, wherein $R_1$ is $C_3$-$C_5$alkyl or $C_5$-$C_6$cycloalkyl; $R_2$ and $R_3$ are each $C_1$-$C_4$alkyl; $R_4$ is hydrogen; $R_5$ is

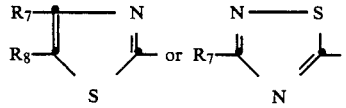

wherein $R_7$ and $R_8$ are each chlorine, bromine or methyl; and Z is —N=C=N—.

5. A compound according to claim 1 of formula

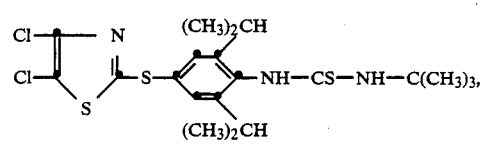

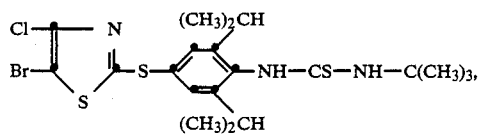

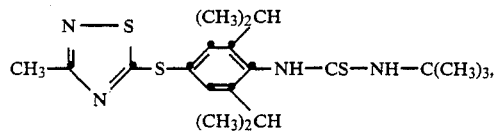

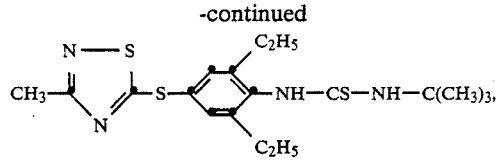

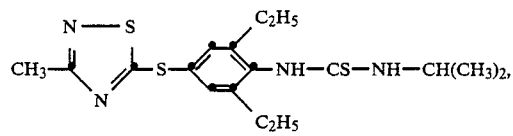

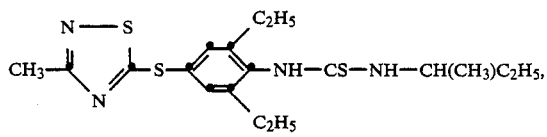

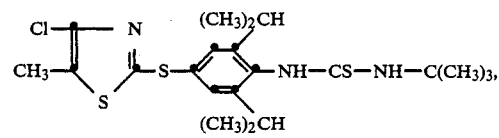

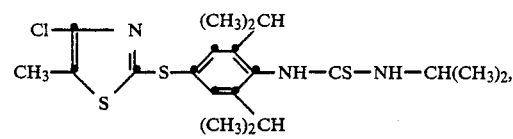

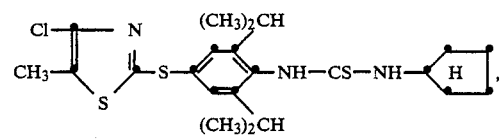

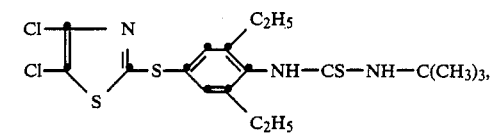

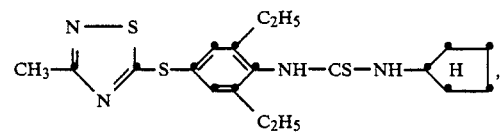

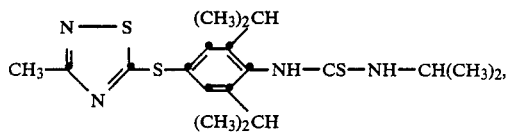

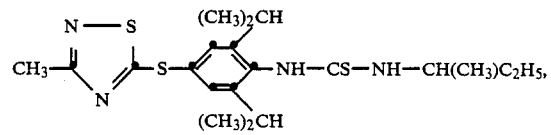

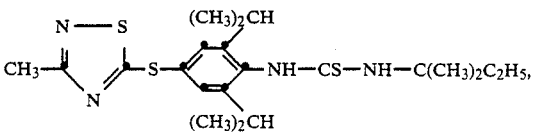

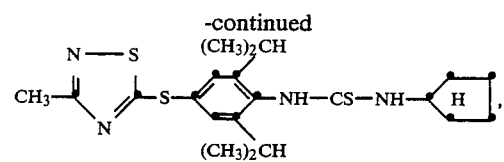
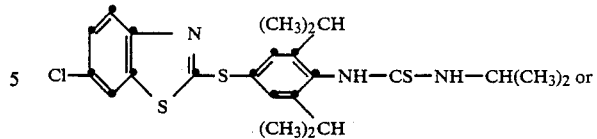
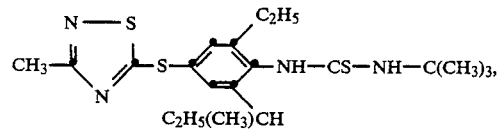
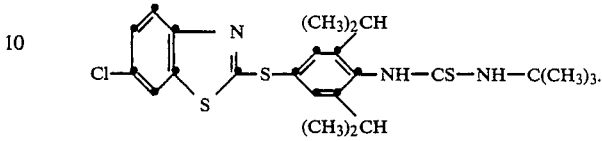
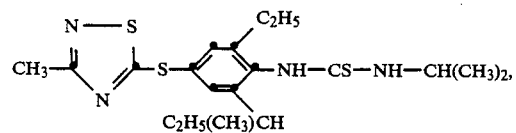
6. A compound according to claim 1 of formula
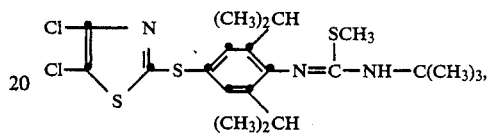
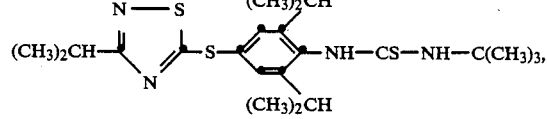
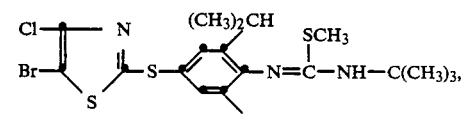
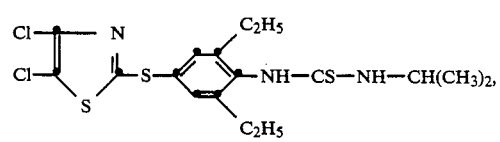
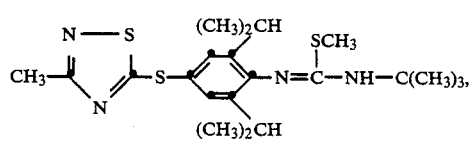
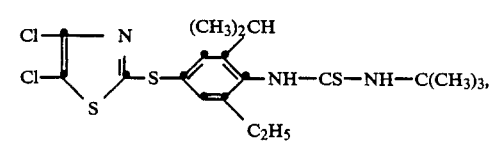
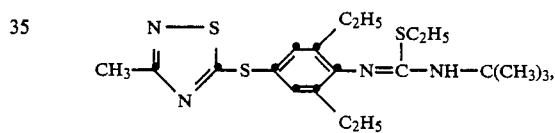
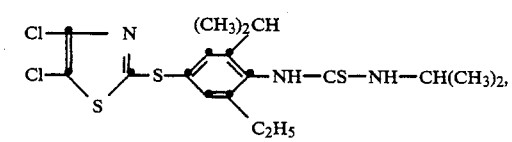
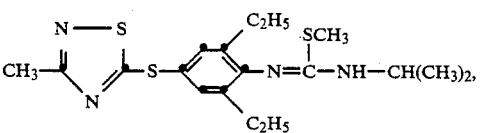
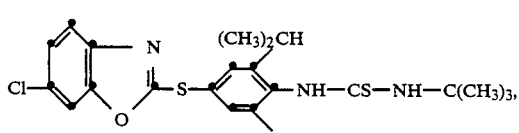
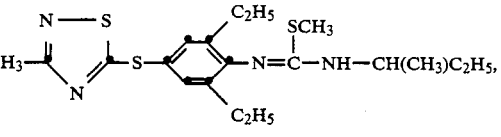
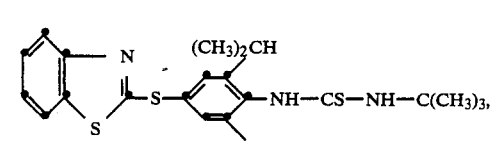
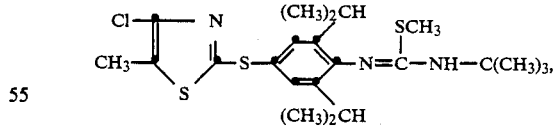
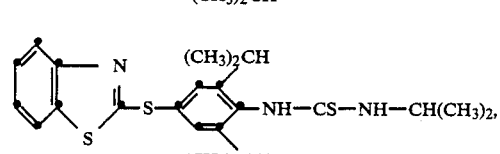
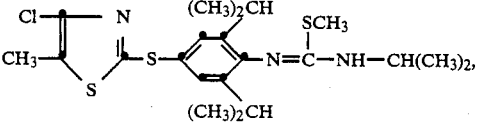
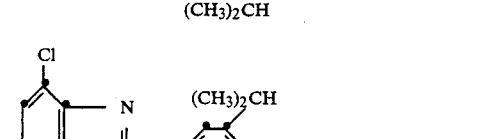
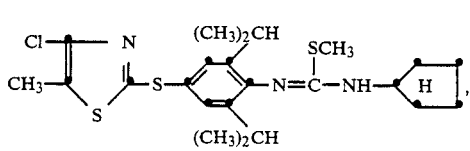

-continued
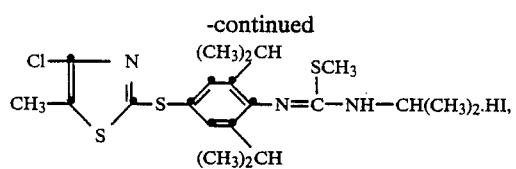
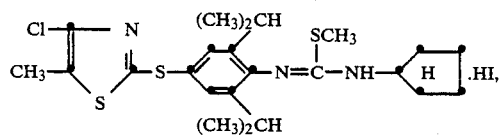
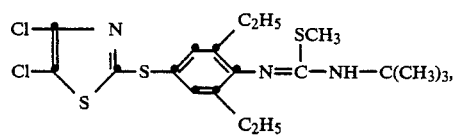
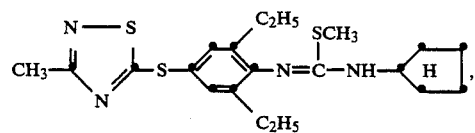
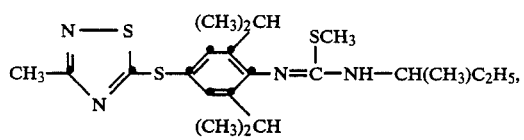
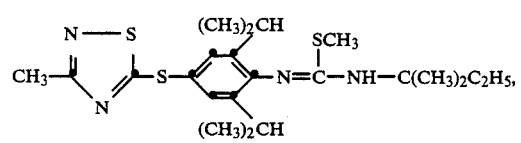
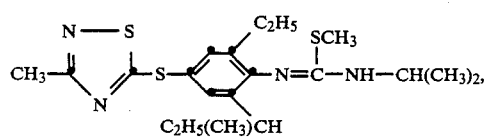
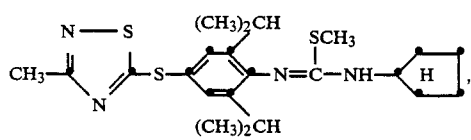
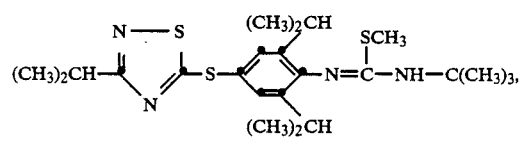
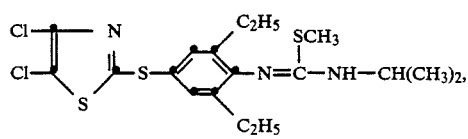
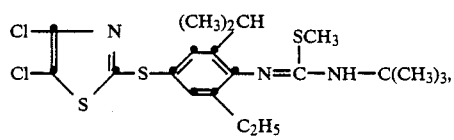
-continued
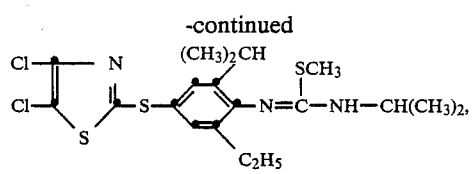
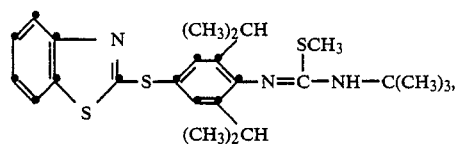
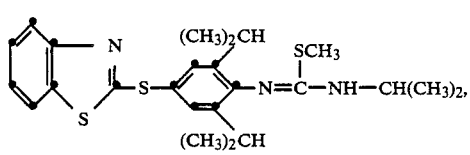
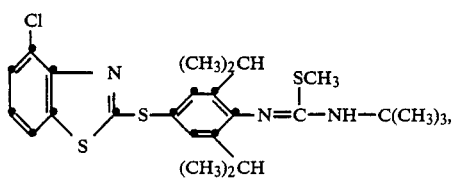
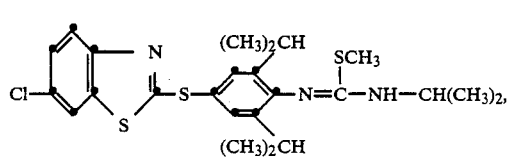
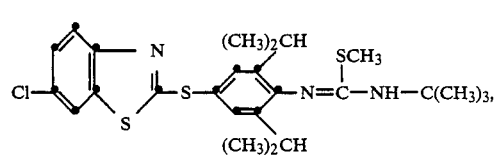
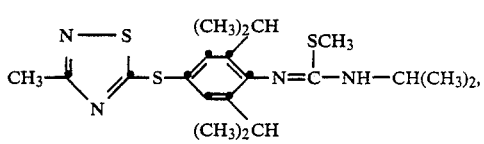
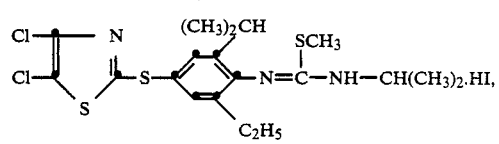
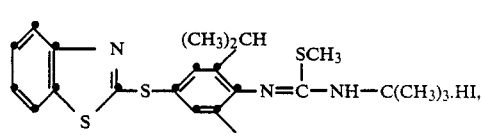
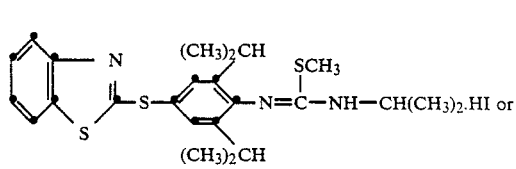

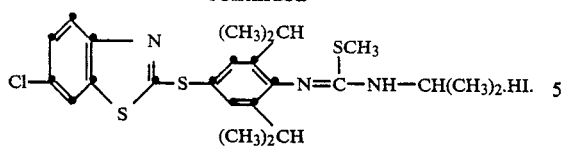
7. A compound according to claim 1 of formula
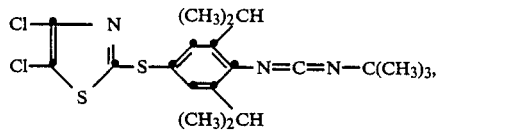
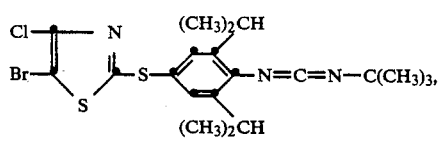
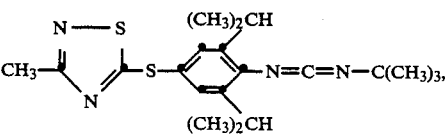
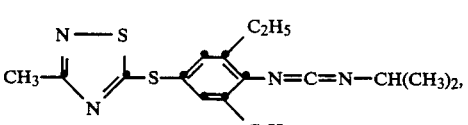
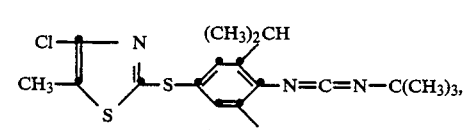
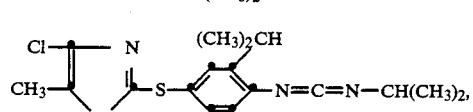
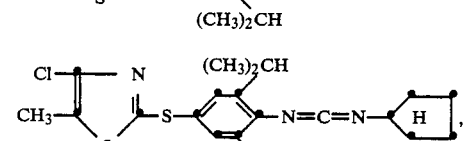
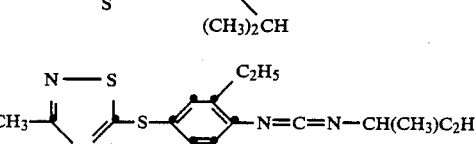
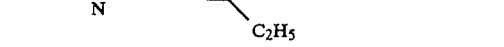
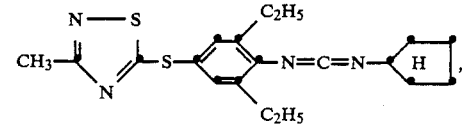
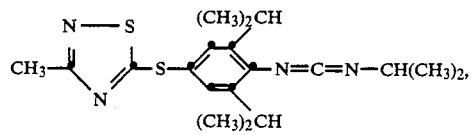
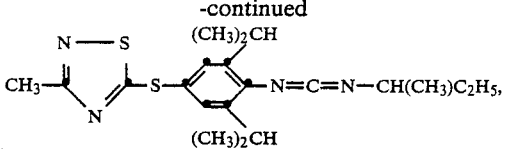
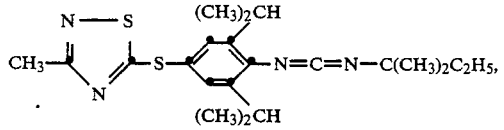
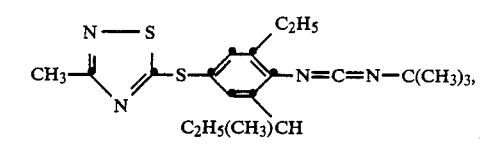
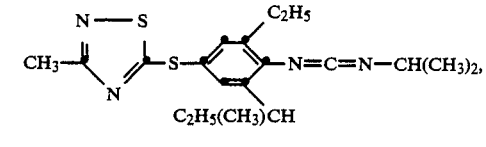
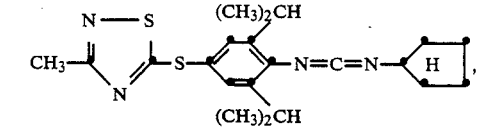
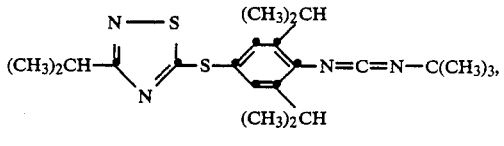
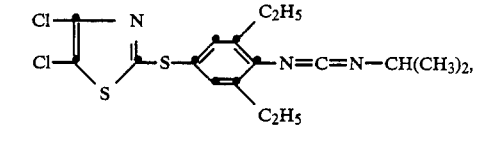
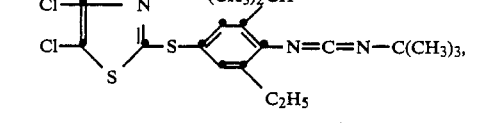
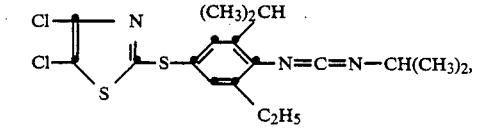
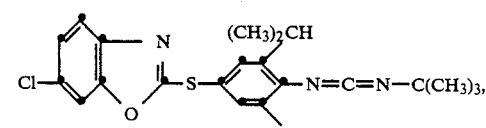
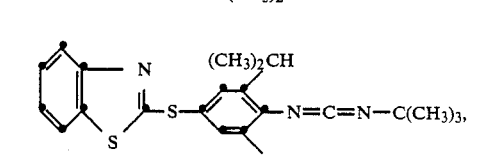

-continued

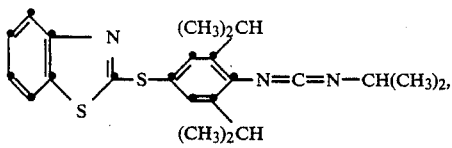

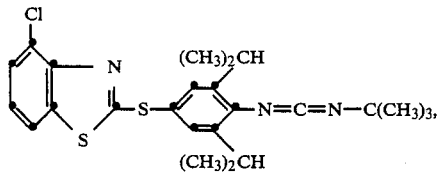

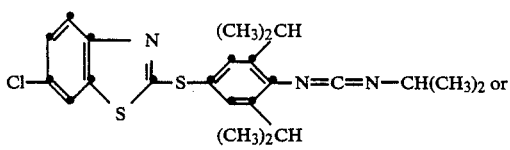

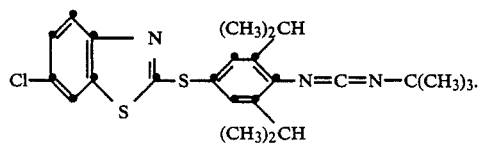

8. A composition which contains, as active component, at least one compound of formula I,

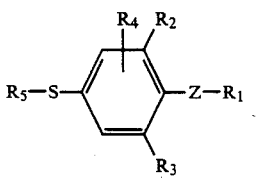

wherein $R_1$ is $C_1-C_7$alkyl, $C_1-C_7$alkyl which is substituted by one ore more halogen atoms and/or $C_1-C_5$alkoxy groups; $C_5-C_6$cycloalkyl, $C_3-C_5$cycloalkyl-$C_1$-$C_3$alkyl or di($C_3-C_5$)cycloalkyl-$C_1$-$C_3$alkyl; $R_2$ is $C_1$-$C_4$alkyl or $C_5-C_6$cycloalkyl; $R_3$ is $C_1-C_4$alkyl; $R_4$ is hydrogen; $R_5$ is

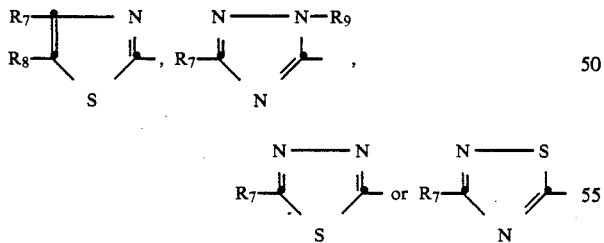

wherein $R_7$ and $R_8$ are each hydrogen, chlorine, bromine, $C_1-C_4$alkyl or $C_1-C_4$haloalkyl, and $R_9$ is $C_1-C_5$alkyl; Z is —NH—CS—NH—, —N=C(SR$_6$)—NH— or —N=C=N—; and $R_6$ is $C_1-C_5$alkyl and a suitable adjuvant therefor.

9. A composition according to claim 8 which contains, as active component, at least one compound of formula I, wherein $R_1$ is $C_3-C_5$alkyl or $C_5-C_6$cycloalkyl; $R_2$ and $R_3$ are each $C_1-C_4$alkyl; $R_4$ is hydrogen; $R_5$ is

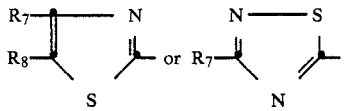

wherein $R_7$ and $R_8$ are each chlorine, bromine or methyl; and Z is —NH—CS—NH—.

10. A composition according to claim 8 which contains, as active component, at least one compound of formula I, wherein $R_1$ is $C_3-C_5$alkyl or $C_5-C_6$cycloalkyl; $R_2$ and $R_3$ each $C_1-C_4$alkyl; $R_4$ is hydrogen; $R_5$ is

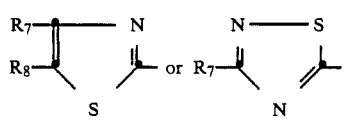

wherein $R_7$ and $R_8$ are each chlorine, bromine or methyl; Z is —N=C(SR$_6$)—NH—; and $R_6$ is methyl or ethyl.

11. A composition according to claim 8 which contains, as active component, at least one compound off formula I, wherein $R_1$is $C_3-C_5$alkyl or $C_5-C_6$cycloalkyl; $R_2$and $R_3$ are each $C_1-C_4$alkyl; $R_4$ is hydrogen; $R_5$ is

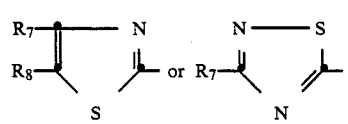

wherein $R_7$ and $R_8$ are each chlorine, bromine or methyl; and Z is —N=C=N—.

12. A method of controlling insect and arachnid pests of animals and plants, which comprises contacting said pests in any one of their different development stages with a compound of formula I

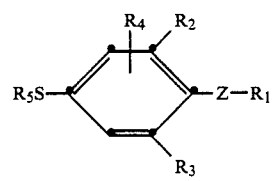

(I)

wherein
$R_1$ is $C_1-C_{10}$alkyl, unsubstituted or substituted by one or more halogen atoms and/or $C_1-C_6$alkoxy groups; $C_3-C_6$alkenyl, $C_3-C_8$cycloalkyl, $C_3-C_8$cycloalkyl which is substituted by one or more halogen atoms and/or $C_1-C_4$alkyl groups; $C_3-C_8$cycloalkyl-$C_1-C_4$alkyl, di($C_3-C_8$)cycloalkyl-$C_1$-$C_4$alkyl; $C_1-C_4$phenylalkyl or $C_1-C_4$phenylalkyl which is substituted in the phenyl nucleus by one or more members selected from the group consisting of halogen, $C_1-C_4$alkyl, $C_1-C_4$alkoxy and/or $C_1-C_4$haloalkyl; or is $C_5-C_6$cycloalkenyl,
$R_2$ is hydrogen, $C_1-C_5$alkyl or $C_5-C_6$cycloalkyl,
$R_3$ is $C_1-C_5$alkyl or $C_5-C_6$cycloalkyl,
$R_4$ is hydrogen or $C_1-C_3$alkyl,
$R_5$ is a heterocycle selected from the group consisting of thiazolyl, 1,2,4-triazolyl, 1,3,4-thiadiazolyl, 1,2,4-thiadiazolyl, 1,3,4-oxadiazolyl, thienyl, benzoxalyl, benzthiazolyl, imidazolyl, furanyl, pyrrolyl, pyrazolyl, oxazolyl, benzofuranyl, indolyl, benzimidazolyl, and tetrazolyl, said heterocycle being unsubstituted or substituted by one or more members selected from the group consisting of halogen, $C_1$-$C_4$alkyl, $C_1$-$C_4$alkoxy, $C_1$-$C_4$halo-alkyl, $C_1$-$C_4$haloalkoxy, $C_1$-$C_4$alkylthio or phenyl, Z is —NH—CS—NH—, —N=C(SR$_6$)—NH— or —N=C=N—, and R$_6$ is $C_1$-$C_5$alkyl, $C_2$-$C_5$alkenyl, $C_3$-$C_4$alkynyl, $C_1$-$C_4$alkoxy-$C_1$-$C_4$alkyl or $C_1$-$C_4$alkylthio-$C_1$-$C_4$alkyl or a salt thereof with an organic or inorganic acid.

* * * * *